US012688580B2

(12) United States Patent
Speter et al.

(10) Patent No.: US 12,688,580 B2
(45) Date of Patent: Jul. 21, 2026

(54) SYSTEMS AND METHODS FOR RECONSTRUCTION OF 3D IMAGES FROM ULTRASOUND AND CAMERA IMAGES

(71) Applicants: Sheba Impact Ltd., Ramat-Gan (IL); Sami Shamoon College of Engineering (R.A), Beer-Sheva (IL)

(72) Inventors: Chen Speter, Kiryat Ono (IL); Doron Manzur, Ramat Gan (IL); Chen Giladi, Beit Hashmonai (IL)

(73) Assignees: Sheba Impact Ltd., Ramat Gan (IL); Sami Shamoon College of Engineering (R.A), Beer-Sheva (IL)

( * ) Notice: Subject to any disclaimer, the term of this patent is extended or adjusted under 35 U.S.C. 154(b) by 207 days.

(21) Appl. No.: 18/286,567

(22) PCT Filed: Apr. 13, 2022

(86) PCT No.: PCT/IL2022/050387
§ 371 (c)(1),
(2) Date: Oct. 12, 2023

(87) PCT Pub. No.: WO2022/219631
PCT Pub. Date: Oct. 20, 2022

(65) Prior Publication Data
US 2024/0193764 A1     Jun. 13, 2024

Related U.S. Application Data

(60) Provisional application No. 63/174,064, filed on Apr. 13, 2021.

(51) Int. Cl.
*G06K 9/00*        (2022.01)
*A61B 8/00*        (2006.01)
(Continued)

(52) U.S. Cl.
CPC ............ *G06T 7/0012* (2013.01); *A61B 8/488* (2013.01); *G06T 7/11* (2017.01); *G06T 7/70* (2017.01);
(Continued)

(58) Field of Classification Search
CPC ........ A61B 2090/367; A61B 2090/378; A61B 5/026; A61B 8/06; A61B 8/0891;
(Continued)

(56) References Cited

U.S. PATENT DOCUMENTS 5,701,898 A     12/1997  Adam et al.
9,456,800 B2 *  10/2016  Anthony .............. A61B 8/4209
(Continued)

FOREIGN PATENT DOCUMENTS

EP        2609868         7/2013
WO    WO 2022/219631    10/2022

OTHER PUBLICATIONS

Supplementary European Search Report and the European Search Opinion Dated Dec. 12, 2024 Fom the European Patent Office Re. Application No. 22787768.5. (7 Pages).
(Continued)

*Primary Examiner* — Hadi Akhavannik

(57)                ABSTRACT

There is provided a method for reconstructing a 3D image, comprising: obtaining Doppler ultrasound images depicting a blood vessel and measurement of blood flow in the blood vessel, and 2D camera images captured by a camera depicting fiducial objects randomly distributed within a viscous material and spaced apart by random distances on a surface of the individual, computing 3D coordinates within a world coordinate system for pixels of the Doppler images using an external reference of an ultrasound transducer pose computed by analysis of relative changes in locations of the fiducial objects within sequential camera images, and com-
(Continued)

puting a respective estimated blood flow for pixels of the Doppler images at locations within the blood vessel, reconstructing a 3D image from 3D voxels computed from the 3D coordinates of pixels of the Doppler images, including respective estimated blood flow, wherein the 3D image depicts the blood vessel and blood flow.

15 Claims, 21 Drawing Sheets

(51) Int. Cl.

| | |
|---|---|
| *G06T 7/00* | (2017.01) |
| *G06T 7/11* | (2017.01) |
| *G06T 7/70* | (2017.01) |
| *G06T 15/00* | (2011.01) |

(52) U.S. Cl.
CPC .... *G06T 15/00* (2013.01); *G06T 2207/10132* (2013.01); *G06T 2207/30104* (2013.01)

(58) Field of Classification Search
CPC ... A61B 8/4254; A61B 8/4281; A61B 8/4416; A61B 8/4444; A61B 8/483; A61B 8/488; G06T 15/00; G06T 2207/10132; G06T 2207/30104; G06T 7/0012; G06T 7/11; G06T 7/70
See application file for complete search history.

(56) References Cited

U.S. PATENT DOCUMENTS

| | | | | |
|---|---|---|---|---|
| 9,538,982 | B2 * | 1/2017 | Anthony | A61B 8/4444 |
| 2004/0034302 | A1 * | 2/2004 | Abovitz | B25J 13/025 |
| | | | | 600/428 |
| 2006/0241461 | A1 | 10/2006 | White et al. | |
| 2016/0113632 | A1 | 4/2016 | Ribes et al. | |
| 2016/0228204 | A1 * | 8/2016 | Quaid | A61B 34/10 |
| 2016/0242744 | A1 * | 8/2016 | Mihailescu | A61B 90/361 |
| 2017/0151021 | A1 * | 6/2017 | Quaid, III | A61B 34/70 |
| 2021/0007707 | A1 * | 1/2021 | Sethuraman | G01S 7/5208 |

OTHER PUBLICATIONS

Sciaky-Tamir et al. "Three-Dimensional Power Doppler (3DPD) Ultrasound in the Diagnosis and Follow-Up of Fetal Vascular Anomalies", American Journal of Obstetrics & Gynecology, XP005228324, 194(1): 274-281, Jan. 2, 2006.

International Preliminary Report on Patentability Dated Oct. 26, 2023 From the International Bureau of WIPO Re. Application No. PCT/IL2022/050387 (8 Pages).

International Search Report and the Written Opinion Dated Sep. 21, 2022 From the International Searching Authority Re. Application No. PCT/II.2022/050387. (15 Pages).

Invitation to Pay Additional Fees and Communication Relating to the Results of the Partial International Search Dated Jul. 20, 2022 From the International Searching Authority Re. Application No. PCT/IL2022/050387. (4 Pages).

Baba "A Low-Cost Camera-Based Transducer Tracking System for Freehand Three-Dimensional Ultrasound Imaging", Thesis in the Department of electrical and Computer Engineering, Presented in Partial fulfillment of the Requirements for the Degree of Master of Applied Science, Concordia University, Montreal, Quebec, Canada, p. 1-67, Apr. 2016.

Bajura et al. "Merging Virtual Objects With the Real World: Seeing Ultrasound Imagery Within the Patient", ACM SIGGRAPH Computer Graphics, 26(2): 203-210, Jul. 1992.

Cenni et al. "The Reliability and Validity of A Clinical 3D Freehand Ultrasound System", Computer Methods and Programs in Biomedicine, 136: 179-187, Published Online Sep. 6, 2016.

Chen et al. "Reconstruction of Freehand 3D Ultrasound Based on Kernel Regression", BioMedical Engineering OnLine, 13(1): 124-1-124-5, Aug. 28, 2014.

Fenster et al. "Three-Dimensional Ultrasound Imaging", Physics in Medicine and Biology, 46(5): R67-R99, May 2001.

Geatrex "Ultrasound and Motion Capture Analysis for Pre-Operative Planning in Lower Limb Joint Replacement Surgeries", Thesis Submitted in Partial Fulfillment of the Requirements for the Degree of Doctor of Philosophy, The University of Sheffield, UK, Faculty of Engineering, Department of Mechanical Engineering, p. 1-134, Jul. 2019.

Huang et al. "A Review on Real-Time 3D Ultrasound Imaging Technology", BioMed Research International, 2017(Art.ID 6027029): 1-20, Published Online Mar. 26, 2017.

Huang et al. "Linear Tracking for 3-D Medical Ultrasound Imaging", IEEE Transaction on Cybernetics, 43(6): 1747-1754, Published Online Nov. 18, 2013.

Huang et al. "Whole-Breast Ultrasound for Breast Screening and Archiving", Ultrasound in Medicine & Biology, 43(5): 926-933, Published Online Mar. 7, 2017.

Lee et al. "Analysis of Sagittal Profile of Spine Using 3D Ultrasound Imaging: A Phantom Study and Preliminary Subject Test", Computer Methods in Biomechanics and Biomedial Engineering: Imaging & Visualization, 8(3): 232-244, Published Online Apr. 30, 2019.

Mozaffari et al. "Freehand 3-D Ultrasound Imaging: A Systematic Review", Ultrasound in Medicine & Biology, 43(10): 2099-2124, Published Online Jul. 14, 2017.

Nikolaev et al. "Real-Time Volumetric Ultrasound Imaging Using Free Hand Scanning", Proceedings of the 2018 SPIE Medical Imaging: Ultrasonic Imaging and Tomography, Houston, Texas, USA, Mar. 6, 2018, 10580: 105800E-1-105800E-12, Mar. 6, 2018.

Stolka et al. "Multi-DoF Probe Trajectory Reconstruction With Local Sensors for 2D-to-3D Ultrasound", Proceedings of the 2010 IEEE International Symposium on Biomedical Imaging: From Nano to Macro, Rotterdam, The Netherlands, Apr. 14-17, 2010, p. 316-319, Apr. 14, 2010.

Sun et al. "Probe Localization for Freehand 3D Ultrasound by Tracking Skin Features", International Conference on Medical Image Computing and Computer-Assisted Intervention, MICCAI 2014, LNCS 8674, 17(Pt.2): 365-372, Sep. 14, 2014.

Wen et al. "A Novel Bayesian-Based Nonlocal Reconstruction Method for Freehand 3D Ultrasound Imaging", Neurocomputing, 168: 104-118, Available Online Jun. 17, 2015.

* cited by examiner

TENSOR SEGMENTATION

SYSTEMS AND METHODS FOR RECONSTRUCTION OF 3D IMAGES FROM ULTRASOUND AND CAMERA IMAGES

RELATED APPLICATIONS

This application is a National Phase of PCT Patent Application No. PCT/IL2022/050387 having International filing date of Apr. 13, 2022, which claims the benefit of priority under 35 USC § 119(e) of U.S. Provisional Patent Application No. 63/174,064 filed on Apr. 13, 2021. The contents of the above applications are all incorporated by reference as if fully set forth herein in their entirety.

FIELD AND BACKGROUND OF THE INVENTION

The present invention, in some embodiments thereof, relates to processing of medical ultrasound images and, more specifically, but not exclusively, to reconstruction of 3D medical images from 2D ultrasound images.

Ultrasonography (US) is often considered the safest and most inexpensive technique for clinical analysis and medical intervention. US images are routinely captured as 2D images. Some approaches generate 3D ultrasound images.

SUMMARY OF THE INVENTION

According to a first aspect, a computer-implemented method for reconstructing a 3D image depicting blood flow in a blood vessel of an individual, comprises: obtaining Doppler ultrasound images depicting a blood vessel with blood flowing therein and measurement of blood flow in a region of the blood vessel, and 2D camera images captured by a camera depicting a plurality of fiducial objects randomly distributed within a viscous material and spaced apart by random distances on a surface of a body segment of the individual, wherein the Doppler ultrasound images include at least one Doppler ultrasound image, and the 2D camera images include at least one 2D camera image, computing 3D coordinates within a world coordinate system for pixels of each of the Doppler ultrasound images using an external reference of an ultrasound transducer pose computed by analysis of relative changes in locations of the plurality of fiducial objects within sequential 2D camera images, and computing a respective estimated blood flow for each of a plurality of pixels of the Doppler ultrasound images at a plurality of locations within the blood vessel, reconstructing a 3D image from 3D voxels computed from the 3D coordinates of pixels of the Doppler ultrasound images, including respective estimated blood flow, wherein the 3D image depicts an anatomical image of the blood vessel and depicts blood flow.

In a further implementation form of the first aspect, the 3D coordinates are further computed by correcting for actual scale to the world coordinate system by using a size of the fiducial object and/or by adding information from other sensors selected from a group consisting of: an inertial measurement unit, and another camera.

In a further implementation form of the first aspect, the 3D image further comprises voxels computed from a 3D point cloud or mesh depicting the surface of the body segment of the individual.

In a further implementation form of the first aspect, computing 3D coordinates for pixels of each of the Doppler ultrasound images, comprises: computing a pose of the camera in a camera coordinate system relative to the world coordinate system by analyzing relative changes in locations of the plurality of fiducial objects within sequential 2D camera images, applying a calibrated mapping for mapping pixels of the ultrasound images represented in an ultrasound coordinate system to the camera coordinate system, wherein the calibrated mapping is based on a predefined transformation between the pose of the camera and a pose of an ultrasound transducer, and mapping the pixels of the ultrasound images represented in the camera coordinate system to the 3D coordinates within the world coordinate system.

In a further implementation form of the first aspect, computing the respective estimated blood flow comprises an estimated blood flow computed from the Doppler ultrasound image captured by the ultrasound transducer located at an angle to a vector denoting a direction of the blood vessel in which the blood flow is measured further comprising correcting the estimated blood flow for the angle to obtain an estimated actual blood flow.

In a further implementation form of the first aspect, correcting comprises identifying an elliptical-shaped boundary of the blood vessel, computing a transformation of the elliptical shape to a circle, and applying the transformation for projecting the measured blood flow velocity vector to obtain the actual blood flow.

In a further implementation form of the first aspect, further comprising computing an estimate of a longitudinal axis of the blood vessel based on an aggregation of a plurality of 3D points obtained from respective planes of acquisition of each of a plurality of Doppler ultrasound images, computing a current tangent to the longitudinal axis, and wherein correcting comprises correcting the measurement of blood flow based on an angle between the tangent and a normal to the respective plane of acquisition denoted by the tangent.

In a further implementation form of the first aspect, further comprising computing an estimate of a blood flow within a precalculated 3D artery object and using computational fluid dynamics simulation and 3D points obtained from respective planes of acquisition of each of a plurality of Doppler ultrasound images for computing an estimate of blood flow within the 3D artery object.

In a further implementation form of the first aspect, further comprising: for each respective 3D voxel, storing a plurality of initially estimated blood flow values and a corresponding normal to a plane of the ultrasound transducer at which a respective Doppler US image used to compute the respective initial estimated blood flow is captured, estimating actual blood flow in each voxel based on minimizing a projection error between a recorded blood flow velocity vector and an assumed flow velocity vector.

In a further implementation form of the first aspect, further comprising: obtaining volumetric flow within the blood vessel on a sagittal view at a specific location for a plurality of cardiac cycles, and computing an average volumetric flow over the plurality of cardiac cycles, computing a gamma value denoting a real number in a range of −1 to 1 to correct the average volumetric flow and the estimated actual blood flow, computing a cosine angle by using an inverse of the gamma value, and correcting the average volumetric flow using the cosine angle and a dot product between estimated blood flow and real blood flow.

In a further implementation form of the first aspect, further comprising: alternating between (i) obtaining the Doppler ultrasound images and 2D camera images and (ii) obtaining second images comprising B-mode ultrasound images and 2D camera images, computing in the world coordinate system, 3D coordinates for pixels of each of the B-mode ultrasound images, wherein reconstructing the 3D image comprises reconstructing the 3D image from 3D voxels in the world coordinate system computed by aggregating the 3D coordinates of pixels of the B-mode ultrasound images and the Doppler ultrasound images including respective estimated blood flow, wherein the 3D image depicts the anatomical image of the blood vessel created from the aggregation of 3D voxels obtained from pixels of the B-mode and depicts the blood flow in association with the 3D voxels obtained from pixels of the B-mode.

In a further implementation form of the first aspect, the respective estimated blood flow is depicted as color coding of the 3D voxels of the 3D image corresponding to the plurality of locations within the blood vessel, wherein pixels of the Doppler ultrasound images are color-coded denoting blood flow, and further comprising segmenting the colored pixels, wherein the 3D image is reconstructed from 3D voxels corresponding to the segmented color pixels.

In a further implementation form of the first aspect, the respective estimated blood flow of the 3D voxels is selected as maximal values over an imaging time interval during which the Doppler ultrasound images depicting a region within the blood vessel corresponding to the 3D voxels is captured.

In a further implementation form of the first aspect, a plurality of Doppler ultrasound images used to compute the 3D voxels are captured over an imaging time interval depicting variation in blood flow, and wherein the reconstructed 3D image includes, for the 3D voxels, a respective indication of variation in blood flow over the imaging time interval.

In a further implementation form of the first aspect, the reconstructed 3D image is presented as a video over an imaging time interval by varying the indication of blood flow corresponding to the 3D voxels over the imaging time interval.

According to a second aspect, a computer-implemented method for segmenting a 3D image reconstructed from 2D ultrasound images depicting a body segment of an individual, comprising: obtaining 2D ultrasound images depicting a common region of a body segment, and 2D camera images captured by a camera depicting a plurality of fiducial objects randomly distributed in 3D within a viscous material and spaced apart by random distances on a surface of the body segment, computing a plurality of 3D voxels having 3D coordinates within a world coordinate system assigned to pixels of each of the 2D ultrasound images using an external reference of an ultrasound transducer pose computed by analysis of relative changes in locations of the plurality of fiducial objects within sequential 2D camera images, and reconstructing a 3D image from the plurality of 3D voxels, and for each 3D voxel, storing a multi-dimensional sparse dataset mapping between the pose of the ultrasound transducer and intensity values obtained at the 3D coordinates corresponding to the respective 3D voxel and the respective pose of the ultrasound transducer, clustering the plurality of 3D voxels into a plurality of clusters according to a distribution of the multi-dimensional datasets of the plurality of 3D voxels, and segmenting the 3D image according to the plurality of clusters.

In a further implementation form of the second aspect, further comprising correcting the 3D voxels for actual scale to the world coordinate system by using a size of the fiducial object and/or by adding information from other sensors selected from a group consisting of: an inertial measurement unit, and another camera.

In a further implementation form of the second aspect, computing 3D coordinates for pixels of each of the 2D ultrasound images, comprises: computing a pose of the camera in a camera coordinate system relative to the world coordinate system by analyzing relative changes in locations of the plurality of fiducial objects within the sequential 2D camera and correcting for actual scale to the world coordinate system by using the size of the fiducial object and/or by adding information from other sensors selected from a group consisting of: an inertial measurement unit, and another camera, and applying a calibrated transformation for mapping pixels of the 2D ultrasound images represented in an ultrasound coordinate system to the camera coordinate system, wherein the calibrated mapping is based on a predefined relationship between the pose of the camera and a pose of the ultrasound transducer capturing the 2D ultrasound images, and mapping the pixels of the 2D ultrasound images represented in the camera coordinate system to the 3D coordinates within the world coordinate system.

In a further implementation form of the second aspect, the clustering is performed based on manifold learning techniques for discovering similar voxels in a region with respect to some computed distribution of values such as color, intensity surrounding texture.

In a further implementation form of the second aspect, the clustering is performed by clustering the plurality of 3D voxels according to similar patterns of changes in captured ultrasound data for different angles and/or distances of locations corresponding to the respective voxels relative to an ultrasound transducer.

In a further implementation form of the second aspect, 3D voxels in each respective cluster indicate a respective tissue type that creates a respective similar pattern of change in captured ultrasound data for different angles and/or distances relative to the ultrasound transducer.

According to a third aspect, a computer-implemented method for reconstructing a 3D image of a surface and interior of a body segment of an individual, comprises: obtaining 2D ultrasound images depicting tissue in the body segment of the individual and 2D camera images captured by a camera depicting a plurality of fiducial objects randomly distributed in 3D within a viscous material and spaced apart by random distances on a surface of the body segment and depicting the surface of the body segment, computing in a common coordinate system, 3D coordinates for pixels of each of the 2D camera images and 3D coordinates for pixels of each of the 2D ultrasound images, based on an analysis of relative changes in locations of the plurality of fiducial objects within sequential 2D camera images, and reconstructing a 3D image from 3D voxels in the common coordinate system computed by aggregating the 3D coordinates of the 2D camera images and of the 2D ultrasound images, wherein the 3D image depicts the surface of the body segment and tissues within the body segment located relative to the surface of the patient, wherein the reconstructed 3D image comprises at least one reconstructed 3D image.

In a further implementation form of the third aspect, the at least one reconstructed 3D image with additional layers of information including at least one of Doppler and B-Mode, depicts tissues selected in any compatible ultrasound organ scanning procedure, including at least one of: blood vessels, organs, joints, bones, cartilage, non-blood fluid filled cavities, liver gallbladder, thyroid, and fuses the tissues into one whole organ or part of an organ.

In a further implementation form of the third aspect, further comprising correcting the 3D coordinates for actual scale to the world coordinate system by using a size of the fiducial object and/or by adding information from other sensors selected from a group consisting of: an inertial measurement unit, and another camera.

In a further implementation form of the third aspect, the common coordinate system is a real-world coordinate system depicting real-world distances and locations, wherein the 3D image depicts the surface of the body segment and tissues within the body segment using in real-world coordinates, distances, and relative locations.

In a further implementation form of the third aspect, computing in a common coordinate system comprising: computing a pose of the camera in a camera coordinate system relative to the common coordinate system by analyzing relative changes in locations of the plurality of fiducial objects within sequential 2D camera images and correcting for actual scale to world coordinate system by using a size of the fiducial object and/or by adding information from other sensors selected from a group consisting of: inertial measurement unit, and another camera, mapping pixels of the 2D camera images depicting the surface of the body to 3D coordinates within the common coordinate system, applying a calibrated transformation for mapping pixels of the 2D ultrasound images represented in an ultrasound coordinate system to the camera coordinate system, wherein the calibrated mapping is based on a predefined relationship between the pose of the camera and a pose of an ultrasound transducer capturing the 2D ultrasound images, and mapping the pixels of the 2D ultrasound images represented in the camera coordinate system to 3D coordinates within the common coordinate system.

In a further implementation form of the third aspect, further comprising: iterating the obtaining the ultrasound and camera images at a common region of the body segment, and iterating the computing in the common coordinate system, wherein iterating the reconstructing the 3D image comprises iteratively updating a previous 3D image of a previous iteration with 3D voxels computed in a current iteration to obtain an updated 3D image having a higher resolution than the previous 3D image.

In a further implementation form of the third aspect, further comprising: receiving a 3D anatomical image depicting the body segment, the 3D anatomical image captured by another 3D imaging modality device, and registering between the 3D anatomical image and the reconstructed 3D image according to features extracted from the surface of the body segment.

According to a fourth aspect, a viscous material including at least a portion of fluid comprising a plurality of fiducial objects randomly distributed therein in three dimensions (3D) and spaced apart by random distances, for application to a surface of a body of a subject, the plurality fiducial objects sized and having a contrast relative to the viscous material for being depicted by a 2D camera image and used for computation of 3D coordinates that are assigned to pixels of 2D ultrasound images for obtaining 3D voxels used for estimating the pose of an ultrasound transducer.

In a further implementation form of the fourth aspect, further enabling for computing a reconstruction of a 3D ultrasound image depicting any one of an interior of the body or the surface of the patient body region.

In a further implementation form of the fourth aspect, the viscous material comprises an ultrasound gel, wherein the 3D image is reconstructed from 2D ultrasound images captured by ultrasound energy transmitted through the ultrasound gel.

In a further implementation form of the fourth aspect, the plurality of fiducial objects have a small size selected for and/or are made out of an acoustic material selected for not being depicted in the 2D ultrasound images transmitted through the ultrasound gel.

In a further implementation form of the fourth aspect, the plurality of fiducial objects are non-fixed in a specific location within the viscous material and flow within the viscous material in response to a movement of the viscous material.

In a further implementation form of the fourth aspect, the size of each of the plurality of fiducial objects is about 0.5 to 1 millimeter.

In a further implementation form of the fourth aspect, the plurality of fiducial objects is made of a material that is visually enhanced in response to ultraviolet light.

In a further implementation form of the fourth aspect, the plurality of fiducial objects is made of fluorescent material.

In a further implementation form of the fourth aspect, the plurality of fiducial objects is sphere-shaped.

In a further implementation form of the fourth aspect, a density of the plurality of fiducial objects within the viscous material is about 1-1000 per milliliter.

According to a fifth aspect, method of treating a vascular pathology in an individual, comprising: applying a viscous material including at least a portion of fluid comprising a plurality of fiducial objects randomly distributed in 3D and spaced apart by random distances, to a surface of a body segment of an individual at a location corresponding to a blood vessel of interest, maneuvering a probe of an ultrasound transducer with an add-on component including at least one camera, along the surface of the body for simultaneously capturing ultrasound images of the blood vessel within the body and camera images depicting the surface of the body segment and depicting the plurality of fiducial objects, analyzing a reconstruction of a 3D image of the blood vessel and the surface of the body segment located within a common 3D coordinate system representing real-world coordinates, diagnosing the vascular pathology based on the reconstruction of the 3D image of the blood vessel relative to the surface of the body segment, and treating the vascular pathology during an open surgical and/or catheterization procedure.

In a further implementation form of the fifth aspect, further comprising re-maneuvering the probe over the surface of the body for simultaneously capturing ultrasound images of the blood vessel depicting the treated vascular pathology and analyzing the treated vascular pathology in another 3D reconstruction of the blood vessel created from the ultrasound images and the camera images captured during the re-maneuvering of the probe and re-treating the treated vascular pathology when the treated vascular pathology is determined to require another treatment procedure based on another 3D reconstruction.

In a further implementation form of the fifth aspect, further comprising repeatedly maneuvering the ultrasound transducer within a sub-region of the surface corresponding to the vascular pathology at an axial and/or longitudinal orientation of the ultrasound transducer to capture a plurality of ultrasound images of the vascular pathology at different angles and distances, wherein a resolution of the vascular pathology in the 3D image increases with an increased number of maneuvers of the ultrasound transducer over the sub-region.

In a further implementation form of the fifth aspect, the 3D image is segmented according to tissue type, and further comprising analyzing segmentation of the 3D image to determine the effectiveness of the vascular treatment.

In a further implementation form of the fifth aspect, diagnosing the vascular pathology based on the reconstruction of the 3D image of the blood vessel relative to the surface of the body segment, is further based on the blood flow of the blood vessel depicted by the 3D image.

In a further implementation form of the fifth aspect, the treatment is selected from a group consisting of a stent delivered by a catheter, balloon inflation, ablation, drug injection, and manual surgical excision and/or repair.

According to a sixth aspect, a calibration device for calibration of a transformation mapping applied to camera images captured by a camera located at a fixed orientation relative to an ultrasound transduction and ultrasound images captured by the ultrasound transducer, comprises: a single compartment having a circular shaped top surface comprising an ultrasound permeable ultrasonography medium, and a ground truth pattern arranged externally to an outer perimeter of the circular shaped top surface of the compartment, the compartment and ground truth pattern positioned such that when the ultrasound transducer is placed on top of the compartment, the camera captures a camera image of the ground truth pattern, and the ultrasound transducer captures an ultrasound image of an interior of the compartment, from the circular shaped top surface to a bottom surface.

According to a seventh aspect, an add-on to an ultrasound probe, comprises a connector component sized and shaped to connect to a probe of an ultrasound transducer, a first camera housing comprising a first camera, and a second camera housing comprising a second camera, wherein the first camera housing and the second camera housing are each set at a predefined angle relative to a long axis of the connector component, for fixing the first camera and the second camera at predefined angle relative to the ultrasound probe and relative to ultrasound images captured by the ultrasound transducer.

In a further implementation form of the seventh aspect, further comprising an ergonomic holder component that include a grip designed to be held against the palm of the hand of the user, and a ring or trigger like element designed for supporting an index finger of the user.

In a further implementation form of the seventh aspect, the first camera housing and the second camera housing are separated by about 90 degrees perpendicular to the long axis of the connector component.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
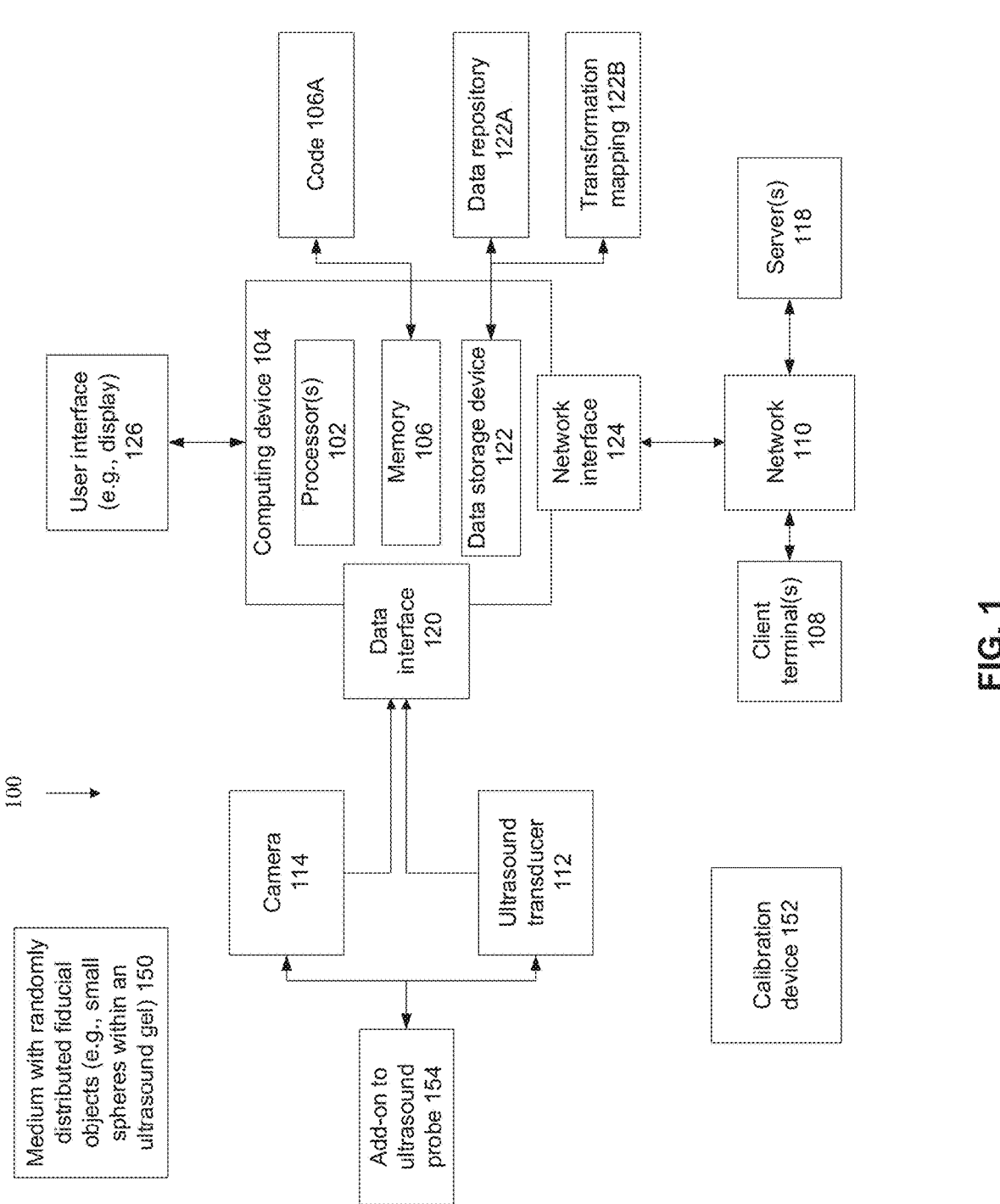
FIG. 1 is a block diagram of components of a system 100 for generating 3D images from ultrasound and camera images based on an analysis of fiducial objects randomly distributed in a viscous material, in accordance with some embodiments of the present invention in accordance with some embodiments of the present invention.

The present invention, in some embodiments thereof, relates to processing of medical ultrasound images and, more specifically, but not exclusively, to reconstruction of 3D medical images from 2D ultrasound images.

Embodiments described herein may relate to 3D medical images depicting compatible organs (such as liver, gallbladder thyroid, articulate joints, etc.) for holistic imaging of the hole organ, with or without blood flow, with or without Doppler (e.g., gray scale alone).

Embodiments described herein may relate to 3D medical images depicting one or more blood vessels, for example, femoral artery, carotid artery, aorta, and/or other internal body tissues, for example, organs such as kidney, liver, gallbladder, spleen, and thyroid. The body parts may not necessarily depict blood vessels large enough to be depicted in the images, for example, joints, bones, cartilage, and the like. The body parts may depict body parts that include air, such as air filled organs, for example, lungs, and intestine. The body parts may be fluid filled with fluid that may not necessarily be blood, and/or may not necessarily flow at a rate that is significant, such as non-blood filled cavities, for example, bladder, and abscess.

Embodiments described herein relating to Doppler are a not necessarily limiting example, and other ultrasound imaging modalities may be used alternatively or additionally, for example, B-mode. As used herein, the term Doppler may be interchanged with the term B-mode where relevant.

As used herein, the phrase Doppler ultrasound images refers to at least one Doppler ultrasound image, and the phrase 2D camera images refers to at least one 2D camera image, the phrease reconstructed 3D image refers to at least one reconstructed 3D image, and the like for other images.

An aspect of some embodiments of the present invention relates to a viscous material that includes at least a portion of fluid, optionally an ultrasonography gel, that includes fiducial objects randomly distributed, i.e., in three dimensions, within the viscous material, e.g., ultrasonography gel, and spaced apart by random distances. The fiducial objects may be, for example, small spheres of different colors, having diameters, for example, in the range of 0.5 to 1 millimeters. The viscous material, e.g., ultrasonography gel, is designed for application to a surface of a body of a subject, e.g., skin, for transmitting ultrasonic energy between an ultrasound transducer contacting the surface and internal anatomical structures, for capturing 2D ultrasound images of the interior of the body. The fiducial objects are sized and have a contrast relative to the viscous material, e.g., ultrasonography gel for being depicted by a 2D camera image and used for computation of 3D coordinates that are assigned to 2D ultrasound images, e.g., 3D coordinates assigned to 2D pixels in the 2D ultrasound images, for generating a reconstruction of a 3D ultrasound image depicting the interior of the body.

The blood flow may refer to blood flowing in a vessel, such as an artery and/or a vein. The blood may be flowing, for example, through a stenosis (e.g., as described herein), past a plaque, and/or past the inner walls of the blood vessel. The blood flow may be measured using a velocity, which may indication speed and/or direction of the blood flow. Blood velocity may be measure for example, in centimeters per second. Blood capacity may be measured for the blood flow, for example, in cubic centimeter per second. Direction may be measured, for example, in degrees relative to a baseline, such as relative to a long axis of the blood vessel. Exemplary blood vessels include: carotid artery, aorta, femoral artery, superior and/or inferior vena cava, brachial, renal artery, hepatic artery, and/or other blood vessels in other locations of the body. Other details of blood flow are described herein.

An aspect of some embodiments of the present invention relates to the reconstruction of a 3D image which depicts blood flow in multiple 3D locations of a blood vessel, e.g., throughout the imaged blood vessel. As referred to herein, a 3D image may be described as a 3D point cloud, a meshed 3D object, a graph 3D, and the like. Doppler ultrasound images depicting a blood vessel with blood flowing therein, and a measurement of blood flow in a region of the blood vessel, are obtained. For example, a 2D ultrasound image depicting the blood vessel and measurement of blood velocity for a pixel of the 2D ultrasound image. The image may be a standard B-mode image associated with standard Doppler mode measurements. 2D camera images captured by a camera depicting fiducial objects randomly distributed in 3D within a viscous material, e.g., ultrasonography gel, and spaced apart by random distances on a surface of the body segment, are obtained. The camera images may be simultaneously obtained with the ultrasonography images; for example, the camera is an add-on to an ultrasound probe. 3D coordinates within a world coordinate system depicting real-world distances and location are computed for pixels of each of the Doppler ultrasound images. The world coordinate system defines a scale for the 3D coordinates, which may be in Euclidean space and corresponds to distances and locations in the real world, i.e., no deformations of the space are applied. The scale of the world coordinate system may be 1:1, or another scale, with the real-world distances; for example, a 5 cm distance between the skin and an artery depicted in the image represents a real 5 cm distance in the body of the subject. The 3D coordinates are computed using an external reference of a pose of the ultrasound transducer used to capture the Doppler images. The external reference is computed by analysis of relative changes in locations of the fiducial objects within sequential 2D camera images that are captured as the ultrasound probe is being maneuvered while Doppler images are being captured. The 3D location and/or pose of the 2D camera within the external reference is computed based on the analysis of the relative changes in the location of the fiducial objects. The 3D location and/or pose of the ultrasound transducer is computed from the 3D location and/or pose of the 2D camera, for example, based on a known calibrated fixed transformation between the locations and/or orientations of the camera and the ultrasound transducer. The location of the Doppler images within the external reference is computed according to the location and/or orientation of the camera and the ultrasound transducer. The location of the Doppler images within the external reference are mapped to the world coordinate system by a calibrated mapping function. A correction for the actual scale of the structure and/or motion of the transducer in world units may be obtained by additional information such as estimating the apriori known size of the fiducial objects, for example, the diameter of spheres, and/or by additional information from additional sensors, for example, inertial measurement unit, additional camera and the like. A respective estimated blood flow for multiple pixels of the Doppler ultrasound images multiple locations within the blood vessel is computed. The measured blood flow is corrected to obtain an actual blood flow value by estimating the angle between an ultrasound transducer axis at which the US beams are transmitted and a vector denoting the direction of blood flow in the blood vessel. A 3D image is reconstructed from 3D voxels in the world coordinate system. The 3D voxels are computed by assigning the 3D coordinates to pixels of the Doppler ultrasound images. Each 3D voxel is associated with a respective estimated blood flow. The 3D image depicts an anatomical image of the blood vessel and depicts an indication of blood flow at multiple locations within the blood vessel. For example, different blood velocities may be color-coded, enabling visual presentation of where blood flow in the vessel is fast and/or where blood flow in the vessel is slow. This may enable the diagnosis of vascular pathologies, for example, stenosis when blood flow speeds up within a narrowing of the vessel.

An aspect of some embodiments of the present invention relates to reconstruction of a 3D image which depicts a surface (e.g., skin) and internal body structures of a body segment of an individual, for example, a femoral artery and the skin of the leg. The surface and internal body structures are presented in the same 3D image within the same set of coordinates, enabling visualization of where the internal body structures are located relative to the surface, for example, the location of the femoral artery relative to the skin of the leg. 2D ultrasound images depicting internal tissue in the body segment of the individual are obtained. 2D camera images captured by a camera, depicting the surface of the body segment and depicting fiducial objects randomly distributed in 3D within a viscous material (e.g., ultrasonic gel) and spaced apart by random distances on the surface of the body segment and, are obtained. The camera and ultrasound images may be obtained simultaneously and/or approximately at the same time. 3D coordinates for pixels of the 2D camera images and 3D coordinates for pixels of the 2D ultrasound images are computed in a common coordinate system and/or corrected for scale by using two cameras, and/or by inertial measurement unite or by knowing in advance the average size of the fiducial objects, e.g., spheres. The 3D coordinates are computed based on an analysis of relative changes in locations of the fiducial objects within sequential 2D camera images. 3D voxels are computed by assigning 3D coordinates to the pixels of the camera images and the ultrasound images. A 3D image is reconstructed by calculating the location of the 3D voxel-based to the transducer's movement in the world coordinate frame, which is determined by the use of the movement of the camera relative to the fiducial markers embedded within the ultrasonographic gel. The 3D reconstruction (e.g., 3D image) also depicts the surface of the body segment and tissues within the body segment located relative to the surface. The reconstructed 3D image(s) with additional layers of information including for example, Doppler and/or B-Mode, depicts tissues selected in any compatible ultrasound organ scanning procedure, including at least one of: blood vessels, organs, joints, bones, cartilage, non-blood fluid filled cavities, live gallbladder, thyroid, and fuses the tissues into one whole organ or part of an organ.

An aspect of some embodiments of the present invention relates to segmentation of a 3D image reconstructed from 2D ultrasound images. 2D ultrasound images depicting a common region of a body segment are obtained. 2D camera images captured by a camera depicting fiducial objects randomly distributed in 3D within a viscous material (e.g., ultrasonography gel) and spaced apart by random distances on a surface of the body segment are obtained. The camera and ultrasound images may be obtained simultaneously and/or approximately at the same time. 3D voxels having 3D coordinates within a world coordinate system are computed. The 3D voxels are computed by assigning 3D coordinates to pixels of the 2D ultrasound images using an external reference of the ultrasound transducer pose that captures the ultrasound images. The pose of the ultrasound transducer is computed by analyzing relative changes in locations of the fiducial objects within sequential 2D camera images and/or corrected for scale by using two cameras, and/or by inertial measurement unite or by knowing in advance the average size of the fiducial objects, e.g., spheres. A 3D image is reconstructed from the 3D voxels. For each 3D voxel, a multi-dimensional dataset is computed and stored. The multi-dimensional dataset may be (e.g., is usually) a sparse dataset. As the ultrasound transducer is moved and/or re-oriented, different intensity values are obtained for the same 3D coordinates corresponding to the same 3D voxel for the different poses of the ultrasound transducer. The multi-dimensional dataset maps between the respective pose of the ultrasound transducer and intensity values obtained at the 3D coordinates corresponding to the respective 3D voxel obtained for the respective pose of the ultrasound transducer. The 3D voxels are clustered into multiple clusters according to a distribution of the multi-dimensional datasets of the plurality of 3D voxels. The 3D image is segmented according to subsets of 3D voxel members of each of the clusters. Voxels within each segmented cluster may represent a similar tissue. The clustering may be performed by clustering voxels according to some similarity measure of distribution grayscales and/or colored (e.g., patterns of changes), Doppler values obtained by capturing the ultrasound data from different angles and/or distances of locations corresponding to the respective voxels relative to an ultrasound transducer. Voxels in each respective cluster indicate a respective tissue type that creates a respective similar pattern of change in captured ultrasound data for different angles and/or distances relative to the ultrasound transducer.

When using the ultrasound technology for imaging an organ and the images of the organ, extra noise is recorded, which interferes with the actual images of the organ being imaged. The segmentation approach described herein also increases the signal-to-noise (SNR) ratio of the capture data. When imaging a specific region of the body, multiple images of the same region are obtained. When looking at the same pixel, corresponding to a voxel and/or to 3D locations, from different angles and different distances from the ultrasound probe, each pixel, which is converted to a voxel, is associated with multiple grayscale values, i.e., intensity values, with each pose and distance. Each human tissue, including pathological tissues, may have the same grayscale values recorded from different angles and distances. An optionally unsupervised learning approach, such as Manifold learning, identifies those tissues with the same greyscale values, and the similar greyscale values changes and/or distributions. The same tissue types are segmented optionally on some similarity measures, which define clusters. Similarities between voxels are based on greyscale values and greyscale distributions and may include topological relationships between voxels so that neighboring voxels should be mapped and segmented together in the mapping space. Segmentation of very complicated tissues with higher accuracy and/or precision may be obtained.

An aspect of some embodiments of the present invention relates to treatment of vascular pathology in a blood vessel of an individual. A viscous material, at least a portion of which is fluid, optionally an ultrasonography gel, that includes fiducial objects randomly distributed in 3D and spaced apart by random distances, is applied to a surface of a body segment of an individual at a location corresponding to a blood vessel of interest. A probe of an ultrasound transducer with an add-on component including one or more cameras is maneuvered along the surface of the body, and may include an inertial measurement unite. Ultrasound images of the blood vessel within the body and camera images depicting the surface of the body segment and depicting the fiducial objects are simultaneously captured. A reconstruction of a 3D image of the blood vessel and the surface of the body segment located within a common 3D coordinate system representing real-world coordinates depicting real-world distances and location is generated.

Alternatively or additionally, the 3D image depicts an indication of blood flow (e.g., velocity) at multiple locations within the blood vessel. Alternatively or additionally, the 3D image is segmented into multiple segments, each depicting a respective tissue type, for example, different layers of the wall of the blood vessel, material causing stenosis, and the like. The vascular pathology (e.g., stenosis) is diagnosed based on the reconstruction of the 3D image of the blood vessel relative to the surface of the body segment, and/or based on blood flow patterns within the blood vessel and/or based on the segmented 3D image. The vascular pathology is treated during an open surgical and/or catheterization procedure. The 3D reconstruction (e.g., 3D image) may be used to guide a treatment tool (e.g., catheter).

At least some implementations of the systems, methods, apparatus, and/or code instructions described herein address the technical problem of increasing accuracy of computation of 3D coordinates that are assigned to 2D image elements, e.g., pixels of 2D ultrasound images depicting interior body structures for reconstruction of 3D images using the 3D coordinates, e.g., each 2D pixel is converted to a 3D voxel of the 3D image by calculating the corresponding 3D coordinates. At least some implementations of the systems, methods, apparatus, and/or code instructions described herein improve the technology of reconstructing 3D images from 2D ultrasound imaging data by increasing the accuracy of 3D coordinates assigned to image elements, e.g., pixels, of the 2D ultrasound images. At least some implementations of the systems, methods, apparatus, and/or code instructions described herein provide a solution to the technical problem, and/or the improvement to the technology is provided by fiducial objects randomly distributed, i.e., in 3D, and spaced apart by random distances, within a viscous material, optionally an ultrasonography gel. The fiducial objects are sized and/or have a contrast relative to the viscous material for being depicted by a 2D camera image which is used to compute the 3D coordinates that are assigned to the 2D US images and may help with the correction of the scale of the reconstructed 3D image. The 2D (e.g., monocular RGB) camera may be located as an add-on and/or integrated with the ultrasound probe, capturing images of the ultrasonography gel with fiducial objects therein while the ultrasound probe captures 2D images by transmitting energy through the ultrasonography gel with fiducial objects therein. The small size, the random distribution and/or random spacing, and/or the large density of the fiducial objects provide high textural images required for accurate computation of 3D coordinates. The improvement is over other existing approaches, which are error-prone and/or inaccurate for computation of highly accurate 3D coordinates, for example, using skin features of the skin's surface, temporary tattoo stickers with features, and other costly sensors that sense pose of the probe.

At least some implementations of the systems, methods, apparatus, and/or code instructions described herein address the technical problem of measuring blood flow in multiple locations in a blood vessel using Doppler. At least some implementations of the systems, methods, apparatus, and/or code instructions described herein improve the technology of analyzing Doppler data to measure blood flow and/or improve the technology of reconstruction of 3D images from 2D ultrasound imaging data by generating 3D images of blood vessels that depict blood flow at multiple locations within the blood vessel, using actual estimated blood flow values. At least some implementations of the systems, methods, apparatus, and/or code instructions described herein provide a solution to the technical problem, and/or the improvement to the technology is provided by correcting initial measurements of the blood flow made using Doppler to obtain actual blood flow values. Using standard approaches, a user places the ultrasound probe relative to a long axis of the blood vessel and changes a vector indicator to correct for actual angle as best as possible based on experience and/or "eye-balling it." One or a small number of individual Doppler measurements are made. The improvement provided herein is that actual blood vessel values are computed from the Doppler measured blood values (referred to herein as "correcting") when the angle between the ultrasound transducer and the blood velocity without the need to set the actual blood flow velocity angle manually. Without the need for tedious manual setting up the assumed blood flow angle, the proposed methods calculate the blood flow (e.g., velocity) vector for a large number of locations within the blood vessel, enabling the generation of a visual 3D corrected image of blood flow that visually depicts blood flow along the blood vessel.

At least some implementations of the systems, methods, apparatus, and/or code instructions described herein address the technical problem of improving the visual representation of body structures depicted in 3D images reconstructed from 2D ultrasound images. At least some implementations of the systems, methods, apparatus, and/or code instructions described herein improve the technology of 3D images reconstructed from 2D ultrasound images. At least some implementations of the systems, methods, apparatus, and/or code instructions described herein provide a solution to the technical problem, and/or the improvement to the technology is provided by including imaging data captured by 2D camera images. The imaging data captured by the 2D camera images are included within the same coordinate system used for representing the ultrasound images in the 3D image. The resulting 3D image accurately depicts the location of internal body structures imaged by the ultrasound images relative to surface body structures (e.g., skin) imaged by the camera after correcting for scale, which can be done by integrating additional information such as the average size of spheres within the ultrasonography gel or information from additional sensors, for example, inertial measurement unit or another camera. For example, while performing an invasive procedure on a femoral artery, the user may visually inspect the 3D image to determine where the femoral is located within the leg, improving the tool's guidance into the femoral artery.

At least some implementations of the systems, methods, apparatus, and/or code instructions described herein address the technical problem of segmenting 3D images reconstructed from 2D ultrasonic images. At least some implementations of the systems, methods, apparatus, and/or code instructions described herein improve the technology of image processing by segmenting 3D images reconstructed from 2D ultrasonic images. At least some implementations of the systems, methods, apparatus, and/or code instructions described herein provide a solution to the technical problem, and/or the improvement to the technology is provided by the multi-dimensional dataset that maps between the respective pose of the ultrasound transducer, and intensity values obtained at the 3D coordinates corresponding to the respective 3D voxel obtained for the respective pose of the ultrasound transducer. The 3D voxels are clustered into multiple clusters according to a distribution of the multi-dimensional datasets of the plurality of 3D voxels. The 3D image is segmented according to subsets of 3D voxel members of each of the clusters. Voxels within each segmented cluster may represent a similar tissue. Such segmentation improves over standard segmentation approaches, for example, that are based on visual features in the 2D ultrasound images. Since the same tissues appear differently at different ultrasound transducer poses, the same tissue may be segmented incorrectly using standard approaches. Moreover, since artifacts may be present at some ultrasound transducer poses, the artifacts may reduce the segmentation's ability and/or accuracy. In contrast, as described herein, the same types of tissues are segmented based on the pattern of distribution of intensity values for multiple poses of the ultrasound transducer and may also use neighbors' distribution information, which improves the accuracy of segmenting the same tissue types.

At least some implementations of the systems, methods, apparatus, and/or code instructions described herein address the medical problem of improving vascular pathology diagnosis and/or improving the treatment of vascular pathology. At least some implementations of the systems, methods, apparatus, and/or code instructions described herein improve the field of medicine by improving diagnosis of vascular pathology and/or improving the treatment of vascular pathology. At least some implementations of the systems, methods, apparatus, and/or code instructions described herein provide a solution to the medical problem, and/or the improvement to medicine is provided by the reconstruction of a 3D image that depicts the blood vessel and the surface of the body segment located within a common 3D coordinate system and/or, the 3D image depicting an indication of blood flow (e.g., velocity) at multiple locations within the blood vessel and/or the 3D image which is segmented into multiple segments each depicting a respective tissue type. The 3D image improves the ability of a user to make a diagnosis, e.g., identify stenosis, perform the treatment, e.g., guide a catheter from the skin to the stenosis, and/or evaluate the outcome of the treatment, e.g., check blood flow pattern with a stent in place.

At least some implementations of the systems, methods, apparatus, and/or code instructions described herein address the technical problem of computing a 3D and/or 4D image, in particular, without using radiation, e.g., x-ray. At least some implementations of the systems, methods, apparatus, and/or code instructions described herein improve the technical field of ultrasound imaging, in particular, the technical field of ultrasound images by computing a 3D and/or 4D ultrasound image from 2D ultrasound images by optionally using fiducial objects randomly distributed in an ultrasonography gel (or another viscous medium). The generated 3D and/or 4D images depict a larger tissue region depicted in each 2D ultrasound image by aggregating voxels created by assigning 3D coordinates to pixel intensity values of pixels of the 2D ultrasound images. The generated 3D and/or 4D image may indicate blood flow and/or blood capacity. The 2D ultrasound images may be sequentially acquired, optionally using a standard 2D ultrasound probe. The 2D ultrasound images may be captured as B-mode and/or color mode (Doppler) images.

At least some implementations of the systems, methods, apparatus, and/or code instructions described herein address the technical problem and/or improve the technical field of providing a fixed pattern for being depicted in a camera image captured by a camera associated with an ultrasound transducer, for generating 3D images from ultrasound images captured by the ultrasound transducer. A transformation mapping maps the fixed pattern in the camera image captured by the camera to 3D coordinates assigned to the 2D ultrasound image captured by the ultrasound transducer. The correction of scale for the actual scale of the structure and motion in world units can be recovered by adding the known fiducial markers or by integrating information from additional sensors, for example, an inertial measurement unit or another camera. Other prior approaches used features of the skin itself, e.g., hair, wrinkles, birthmarks, external sensors, e.g., inertial sensor, that measure the pose of the transducer, and/or a temporary tattoo placed on the skin. At least some implementations of the systems, methods, apparatus, and/or code instructions described herein relate to an ultrasonic gel with fiducial objects randomly distributed therein. The fiducial objects may be small enough and/or made out of acoustic material, selected to prevent artifacts on ultrasound images. The fiducial objects may be sufficiently large to be depicted in the camera image. The ultrasonic gel, which is used for capturing the ultrasonic images, also includes the randomly distributed fiducial objects that provide the fixed pattern depicted in the camera image.

At least some implementations of the systems, methods, apparatus, and/or code instructions described herein address the technical and/or medical problem of treating a vascular pathology in a subject. Using standard approaches, the vascular pathology is mapped by sequential 2D ultrasound imaging, optionally in Doppler mode, and/or by performing angiography, e.g., x-ray, CT, MRI, which is an invasive procedure in which contrast material, which may trigger an allergic reaction, and/or may be nephrotoxic, is injected into the vasculature of the subject, and/or where the subject is exposed to high radiation doses, e.g., x-ray angiography, CT angiography. At least some implementations of the systems, methods, apparatus, and/or code instructions described herein improve the technical field and/or medical field of treating a vascular pathology in a subject and/or address the technical and/or medical problem by generating 3D images from 2D ultrasound images, optionally including Doppler, which may be rapidly acquired in a non-invasive fashion without exposing the subject to radiation and/or without injection of contrast material. The 3D image may be captured in real-time, for the guidance of a catheter used to treat the vascular pathology, e.g., by insertion of a stent, balloon expansion, ablation, injection of drugs, and/or other approaches, and/or used to evaluate the vascular pathology before and after treatment. Real-time evaluation post-treatment using the 3D image may help determine whether additional immediate treatment is required and/or whether the treatment has been performed successfully. Follow-up 3D images may be obtained after the treatment for determining whether the treatment is successful over a longer term, or additional treatment is required. Such multiple 3D images to evaluate the treatment cannot be obtained using standard approaches due to the invasive nature of the approaches and/or risk of large amounts of radiation and/or contrast material.

In at least some implementations, the improvement is in the use of the ultrasonography gel, or other viscous material with randomly distributed fiducial objects used for adding more features to the acquired images, thus enabling for more robust and accurate pose estimation of the transducer, which results in more accurate and precise 3D images, the 3D images that depict the internal blood vessels along with the skin in real-world coordinates depicting real-world relative distances and locations, 3D images with corrected blood flow (e.g., velocity, speed) at multiple locations in the vessel, and/or 3D segmentations based on clusters of multi-dimensional datasets corresponding to different voxels locations and distributions and/or mappings between poses of the ultrasound transducer and obtained intensities. Each respective multi-dimensional dataset may be for one set of 3D coordinates corresponding to one voxel and/or group of voxels.

Prior approaches attempted to achieve real-time three-dimensional ultrasound visualization either by using volumetric probes or by routinely moving two-dimensional probes. Medical imaging technologies provide clinical audio-visual information on organs for better clinical and decision making. Thus, medical imaging of the interior of a body is often considered the most pronounced technique for clinical analysis and medical intervention. While medical imaging encompasses a wide range of technologies, the most common tools are X-ray radiography, Computed tomography scan (CT scan), magnetic resonance imaging (MRI), and medical ultrasonography (US).

One of the standard tools for medical imaging is the CT scan. Computed tomography, also known as CT scan, uses a specialized X-ray device to generate a cross-sectional 2D image from a series of 1D X-ray images taken around a single axis of rotation around the object. As the bed passes through the rotating "donut" shape X-ray device, a series of 2D axial images are acquired. Those images can be displayed individually or stacked together to form a 3D model. The CT scan disadvantages are a high degree of radiation exposure, and in some situations, a need for nephrotoxic iodine injection as a contrast material. As opposed to the CT scan, during an MRI procedure, there is effectively zero exposure to ionizing radiation. The MRI technology uses the body's magnetic properties to produce detailed superior 3D images. However, MRIs are very expensive, require a particular room, and cannot be used for patients with implanted metal pieces, claustrophobic patients, and suffers substantially from patient's movements. In a standard ultrasound system, a probe sends high-pressurized frequency waves into the patient's body. As the waves encounter internal organs with different densities, they produce echoes reflected and measured by the probe. Returned echoes are then transformed into an electrical signal, from which an algorithm originated a 2D image. The advantages are the lack of radiation and the injection of hazardous renal contrast. It is also the most cost-effective imaging technique. However, it is regarded as an "operator dependent" device and has the most inferiority quality of imaging since a 3D whole organ image is missing and highly user-dependent.

The use of US technology in the embodiments described herein avoids radiation and contrast, which are currently being used for CT and Angiography examinations, therefore removing the potential hazard for the patient and caregiver from radiation and the prospective patient's renal impairment due to contrast medium.

At least some implementations of the systems, methods, apparatus, and/or code instructions described herein address the above mentioned technical problem and/or improve the above mentioned technical field by generating a 3D ultrasound image without ionizing radiation, without contrast material, that may be captured quickly using a standard US probe, used in patients with implanted metal components, and/or that may depict vascular physiological data such as blood velocity, e.g., centimeters per second, and/or blood capacity, e.g., cubic centimeter per second.

At least some implementations of the systems, methods, apparatus, and/or code instructions described herein generate 3D US images of blood vessels without x-ray radiation and/or without administration of contrast materials. In contrast, standard approaches for capturing angiographic images of blood vessels require administration of contrast material into the vasculature and/or capturing of x-ray images.

At least some implementations of the systems, methods, apparatus, and/or code instructions described herein generate higher-quality 3D US images in comparison to prior approaches. At least some implementations of the systems, methods, apparatus, and/or code instructions described herein generate much more accurate segmentation and/or higher resolution 3D US images by eliminating the different noise sources, which are the downsides of standard US systems.

At least some implementations of the systems, methods, apparatus, and/or code instructions described herein add additional layers of information on the reconstructed 3D US images. The 3D US image may depict one or more of: the velocity of blood flowing through an imaged blood vessel and the capacity of blood flowing through the imaged blood vessel. In contrast, CT or MRI, which are mainly used for vascular imaging due to their abilities, cannot display crucial physiological information as may be measured only by using the Doppler modality of the US system.

At least some implementations of the systems, methods, apparatus, and/or code instructions described herein may be added on and/or connected to, and/or integrated with, existing 2D US acquisition systems.

At least some implementations of the systems, methods, apparatus, and/or code instructions described herein enable inexperienced users to operate the US imaging system and perform a high-quality examination of a patient, which may reduce, e.g., to a minimum, the dependence of the operator.

At least some implementations of the systems, methods, apparatus, and/or code instructions described herein reconstruct the 3D US image depicting a complete image of tissue and/or an organ in comparison to 2D US images and/or other approaches. The reconstructed 3D US image may be registered with other 3D images acquired by other 3D imaging modalities, for example, CT angiography (CTA), MRI angiography (MRA), and the like.

At least some implementations of the systems, methods, apparatus, and/or code instructions described herein address the technical problem of increasing accuracy and/or computational efficiency of computing a pose, e.g., position and/or orientation, of an ultrasound transducer during capture of ultrasound images and/or improve the technical field of computing the pose of the ultrasound transducer during the capture of ultrasound images. The pose of the ultrasound transducer computed for each ultrasound image may be used to reconstruct 3D images, as described herein. The computation of the pose of the ultrasound transducer by mapping a camera image of fiducial objects in an ultrasonography gel or other viscous medium using a calibrated transformation mapping is more accurate and/or cost-effective and less complex and/or more computationally efficient (e.g., requiring fewer processing resources and/or fewer memory resources) in comparison with other approaches, for example, using only an inertial measurement unit, using a camera capturing a natural skin feature, e.g., hairs, birthmarks, optical tracking system, mechanical systems, and optical fibers, magnetic sensors and the like.

At least some implementations of the systems, methods, apparatus, and/or code instructions described herein address the technical problem of reducing the dependence of the operator and/or improving a user experience in performing ultrasound examinations and/or improving the technical field of ultrasound systems designed for use by inexperienced users. The pose of the ultrasound transducer and/or 3D coordinates are computed for ultrasound images using the camera images for different poses of the ultrasound transducer, enabling a non-experienced user to acquired relevant information which can be further analyzed by an expert. The collected data by the non-experienced used is used to reconstruct the 3D image.

At least some implementations of the systems, methods, apparatus, and/or code instructions described herein address the technical problem of creating improved ultrasound images of organs, with relatively reduced noise and/or artifacts, and/or improve the technical field of ultrasound imaging by creating ultrasound images of organs with relatively reduced noise and/or artifacts. Using standard approaches, each 2D ultrasound image is independently captured, and reducing noise and/or artifacts depends on the ability of the user to capture images at optimal poses. In contrast, the 3D images created herein by aggregating 3D voxel data computed from multiple 2D images of the ultrasound transducer from different poses reduce the noise and/or artifacts in the reconstructed 3D image.

At least some implementations of the systems, methods, apparatus, and/or code instructions described herein address the technical problem of creating 3D anatomical images of blood vessels that also depict an indication of blood flow, e.g., velocity and/or capacity, through the blood vessels, and/or improve the field of medical imaging by creating 3D anatomical images of blood vessels that also depict an indication of blood flow through the blood vessels. Standard approaches are designed for one type of data—for example, CT and MRI for generating 3D anatomical images. CT and MRI, which are mainly used for vascular imaging due to their abilities, cannot display crucial physiological information gained by using the Doppler modality of the US system. In contrast, Doppler US is designed for measuring blood flow but does not provide good anatomical images of the blood vessel.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
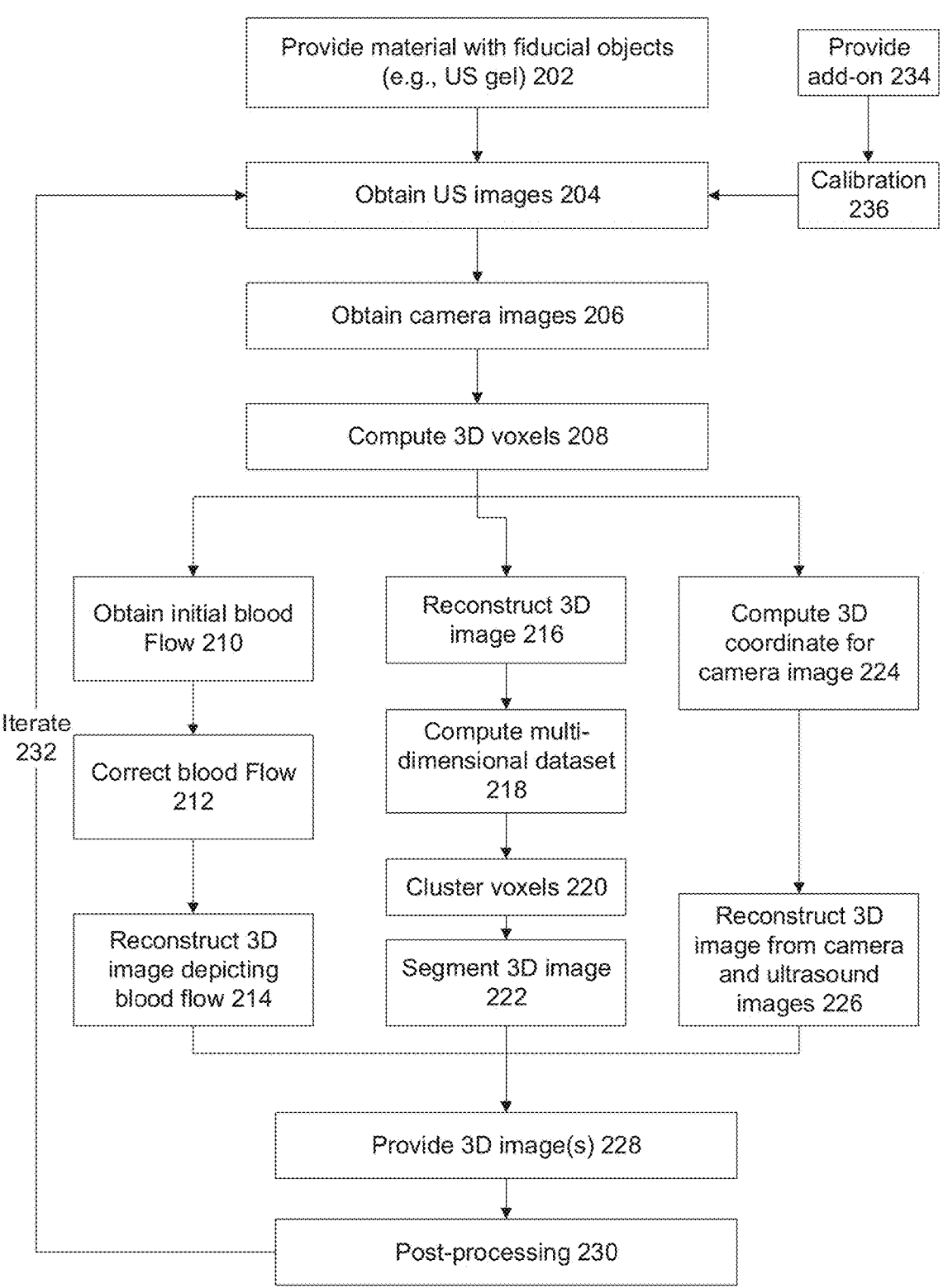
FIG. 2 is a flowchart of a method of generating 3D images from ultrasound and camera images based on an analysis of fiducial objects randomly distributed in a viscous material, in accordance with some embodiments of the present invention in accordance with some embodiments of the present invention.
Figure 3:
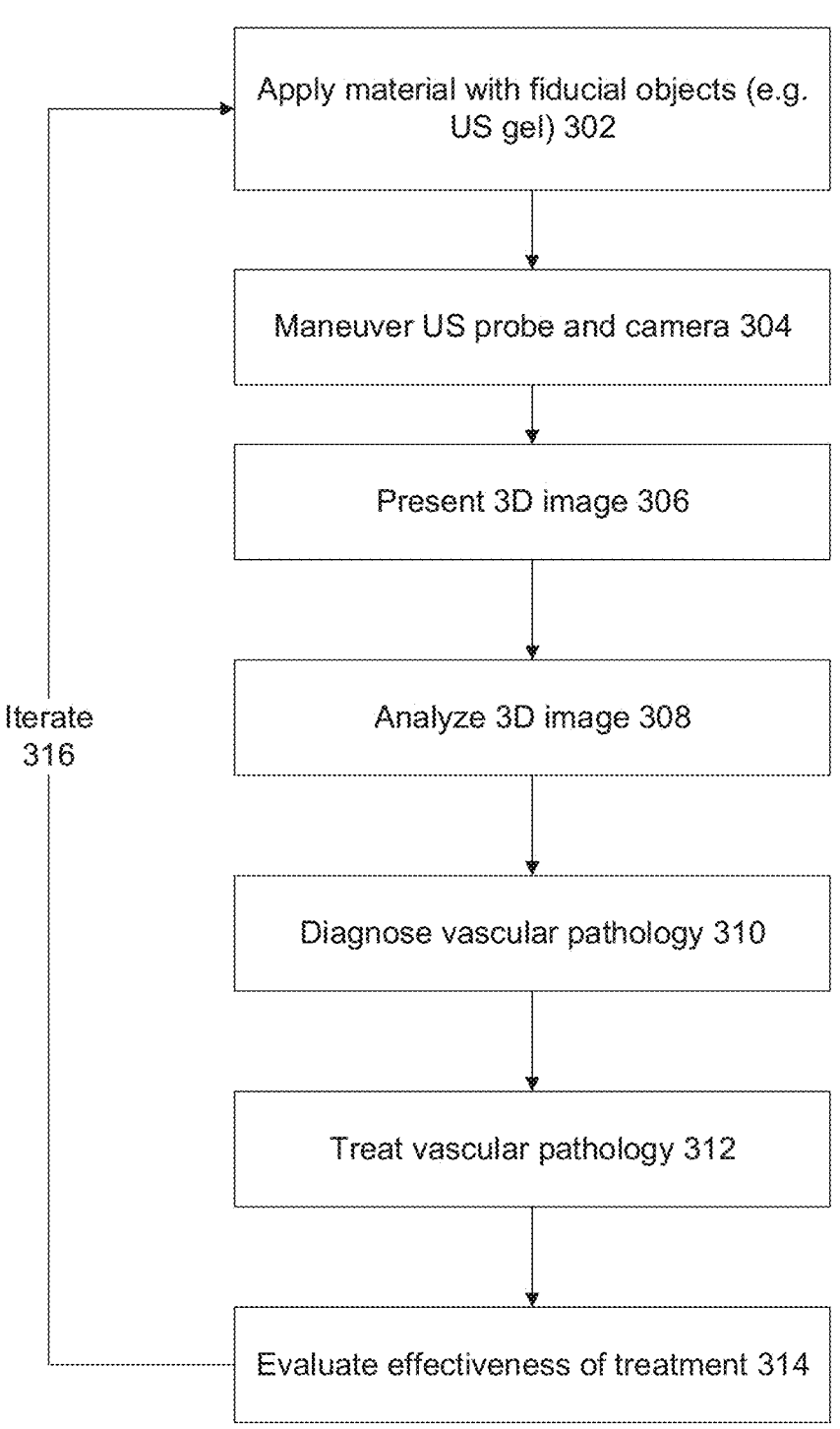
FIG. 3 is a flowchart of a method of diagnosing and/or treating a vascular pathology according to 3D images generated from ultrasound and camera images based on an analysis of fiducial objects randomly distributed in a viscous material, in accordance with some embodiments of the present invention.
Figure 4:
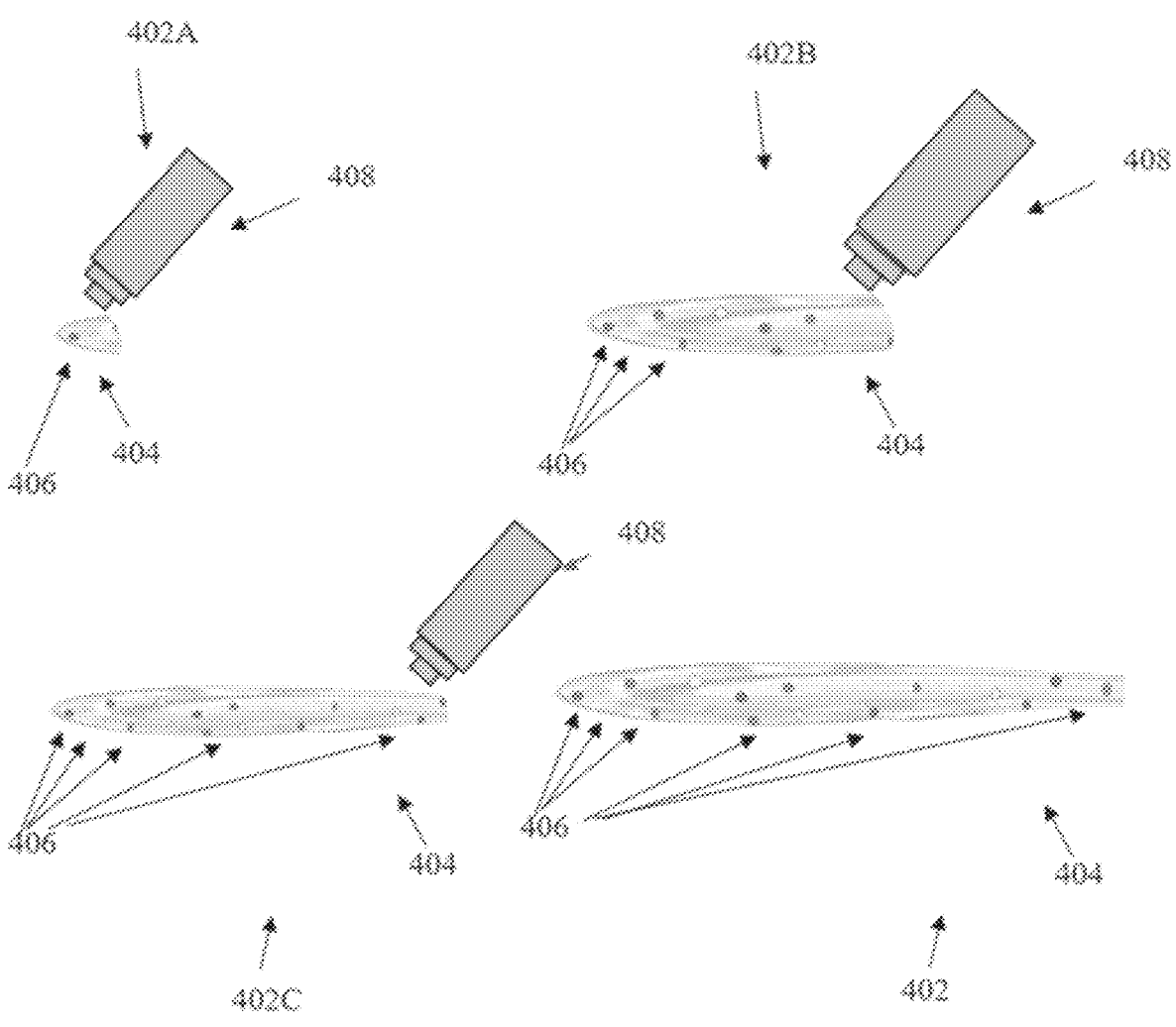
FIG. 4 includes schematics depicting a process of applying an ultrasonic gel with fiducial objects randomly distributed therein for capturing camera images used to reconstruct a 3D image, in accordance with some embodiments of the present invention.
Figure 5:
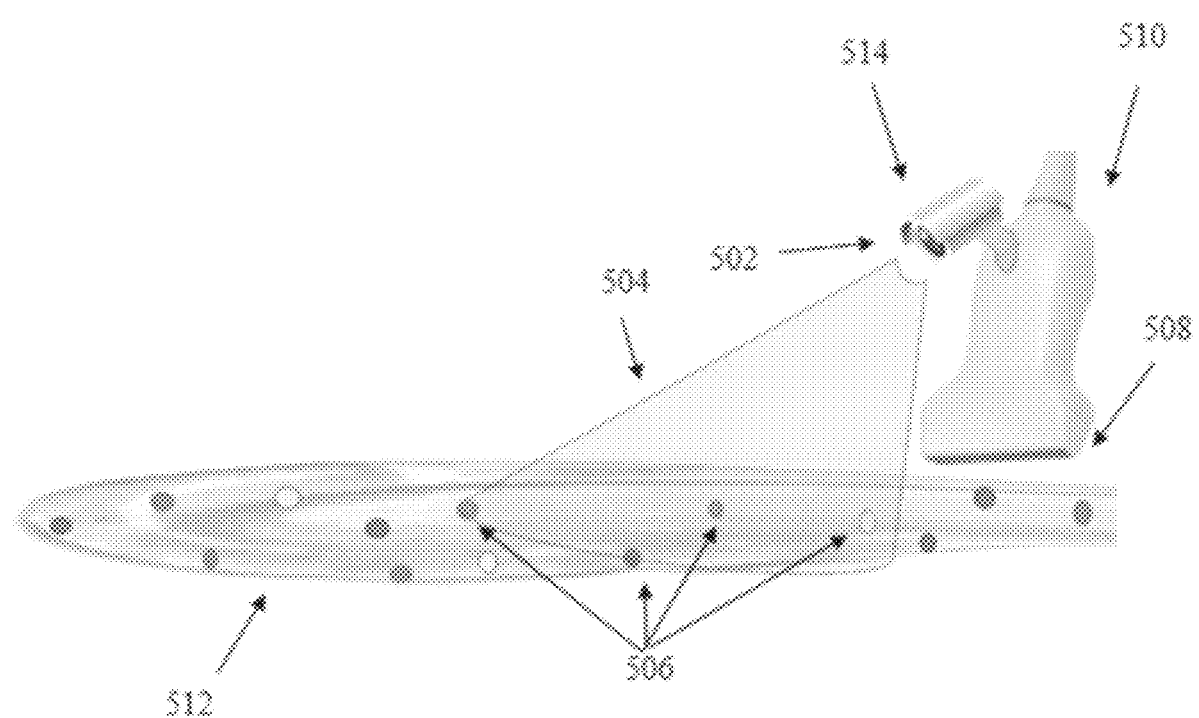
FIG. 5 is a schematic depicting a camera capturing a camera image of fiducial objects randomly distributed within an ultrasonic gel while an ultrasound transducer of an ultrasound probe captures ultrasonic images through the gel, in accordance with some embodiments of the present invention.
Figure 6:
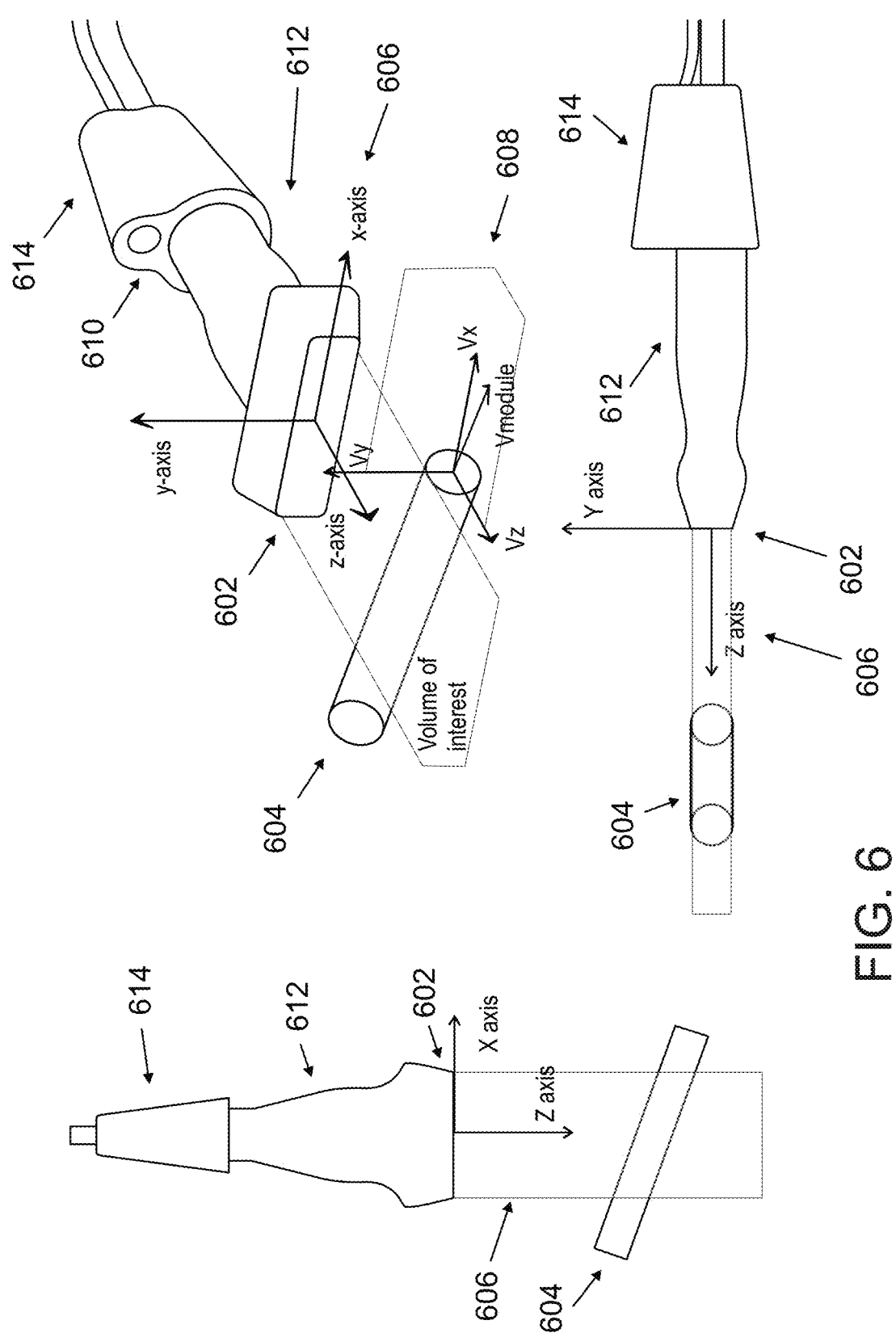
FIG. 6 is a schematic depicting exemplary x,y,z axes of an ultrasound transducer for computing 3D coordinates within a 3D space Vx, Vx, Vz module of a tissue depicted in ultrasound images, in accordance with some embodiments of the present invention.
Figure 7:
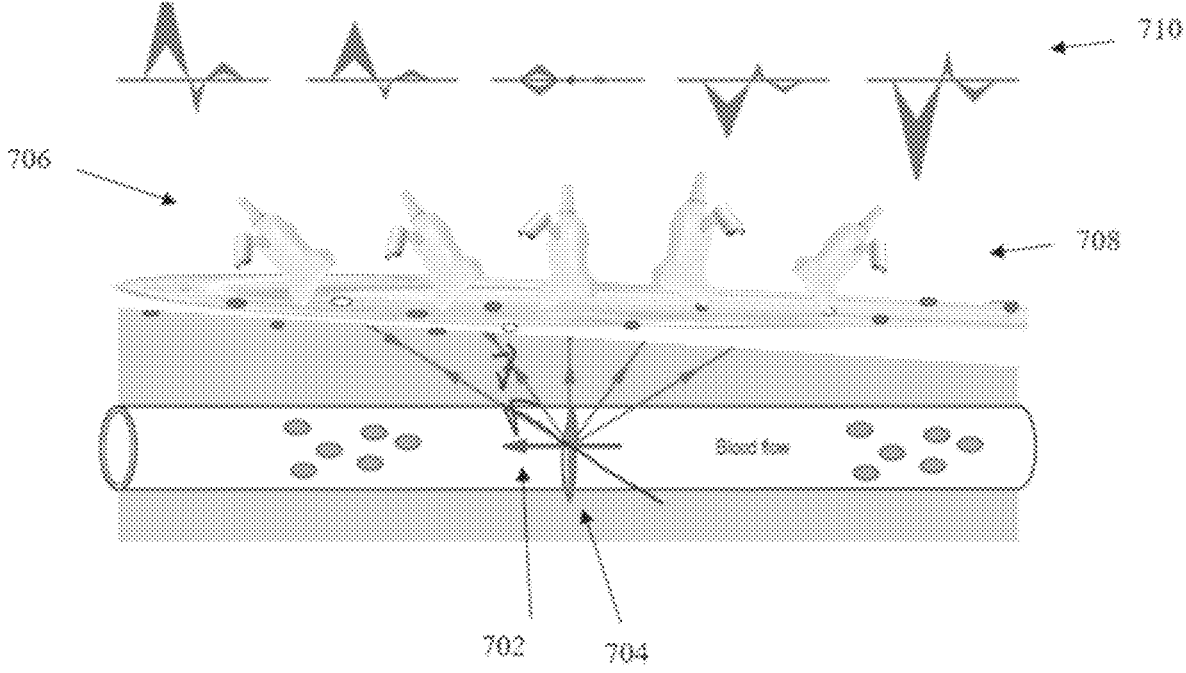
FIG. 7 is a schematic depicting correction of flow of blood within an ultrasound image of a blood vessel obtained by an ultrasound transducer at multiple orientations, in accordance with some embodiments of the present invention.
Figure 8:
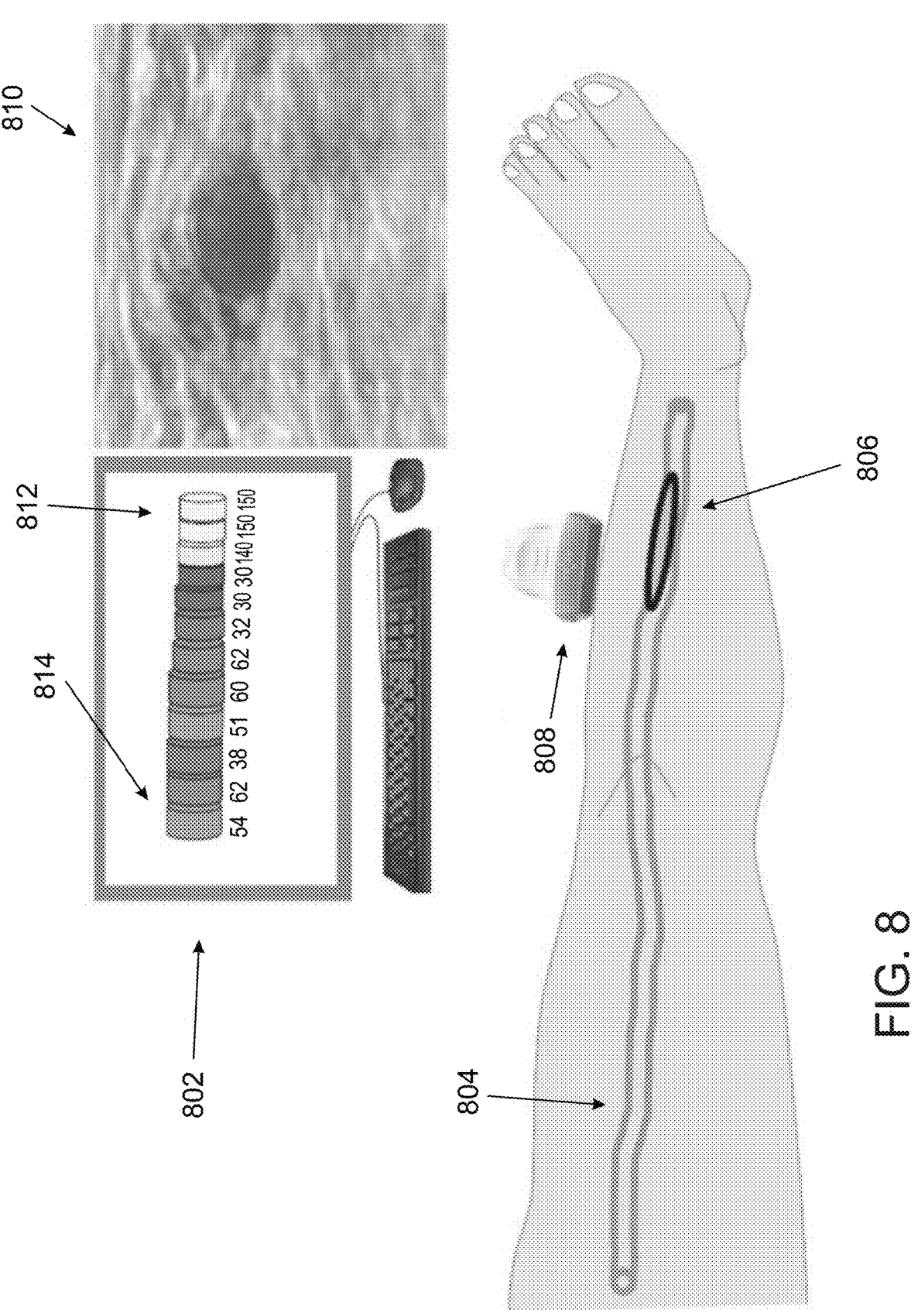
FIG. 8 is a schematic depicting reconstruction of a 3D image including an image of an artery depicting a vascular pathology, e.g., stenosis, and indicating the velocity of blood flow through an artery, in accordance with some embodiments of the present invention.
Figure 9:
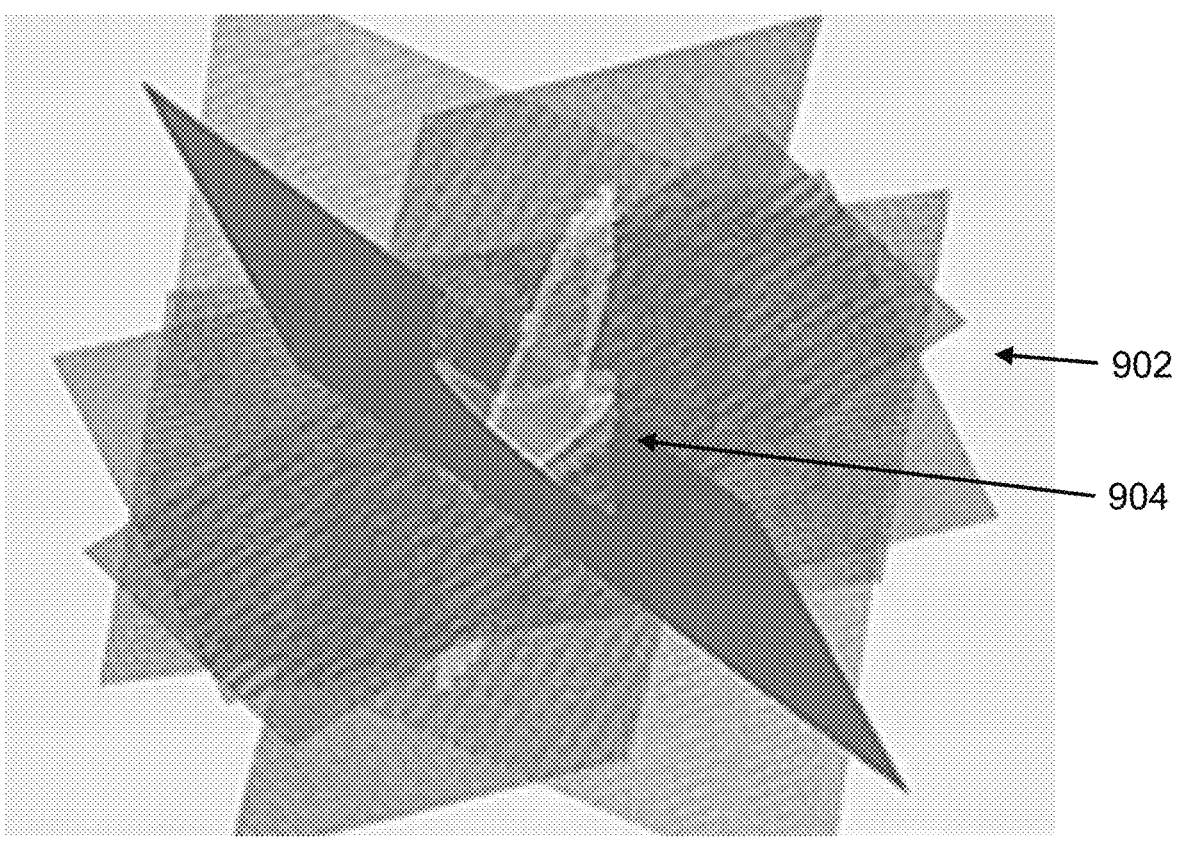
FIG. 9 is a schematic depicting a process of collecting data for one multi-dimensional (optionally sparse) dataset of one set of 3D coordinates corresponding to one voxel and/or group of voxels, in accordance with some embodiments of the present invention.
Figure 10:
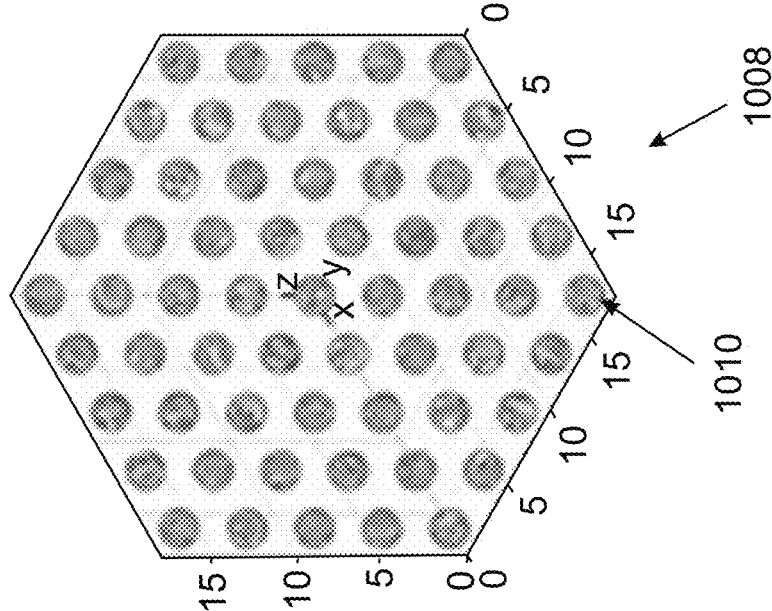
FIG. 10 is a schematic depicting a representation of a multi-dimensional dataset of a certain 3D coordinates of a certain voxel as a sphere with gray colored values depicting different B-Mode grayscale values acquired from various transducer poses, in accordance with some embodiments of the present invention.
Figure 10:
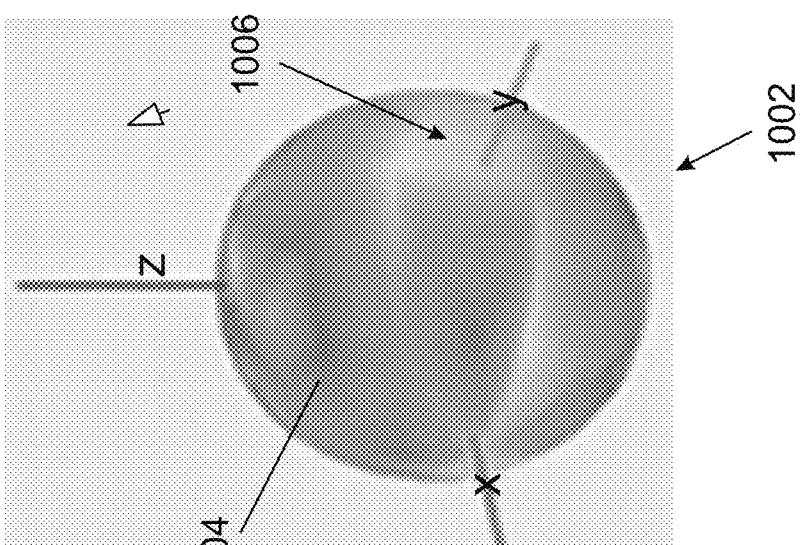
Figure 11:
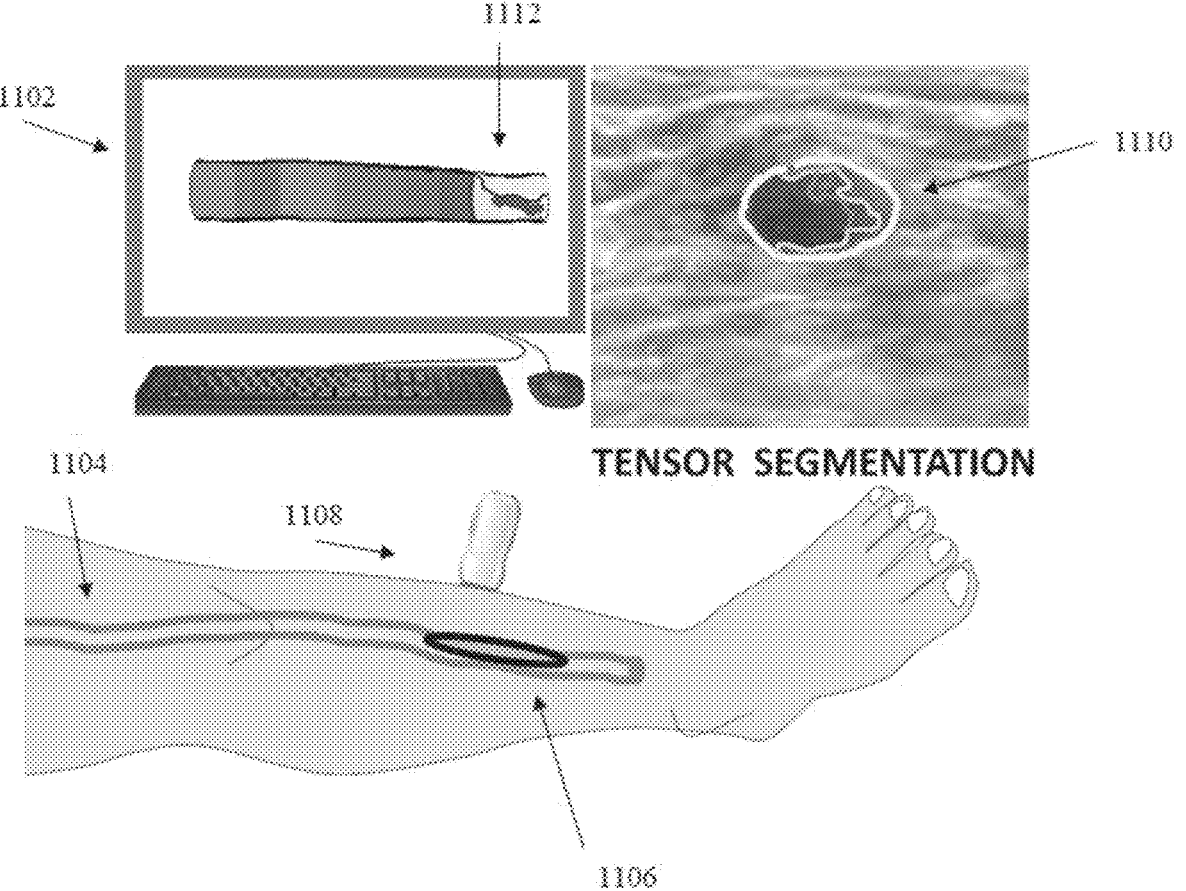
FIG. 11 is a schematic depicting reconstruction of a 3D image based on segmentation of clusters of the (optionally sparse) multi-dimensional datasets, that includes artery segmented into different tissue types and depicting blood flow values, in accordance with some embodiments of the present invention.
Figure 12:
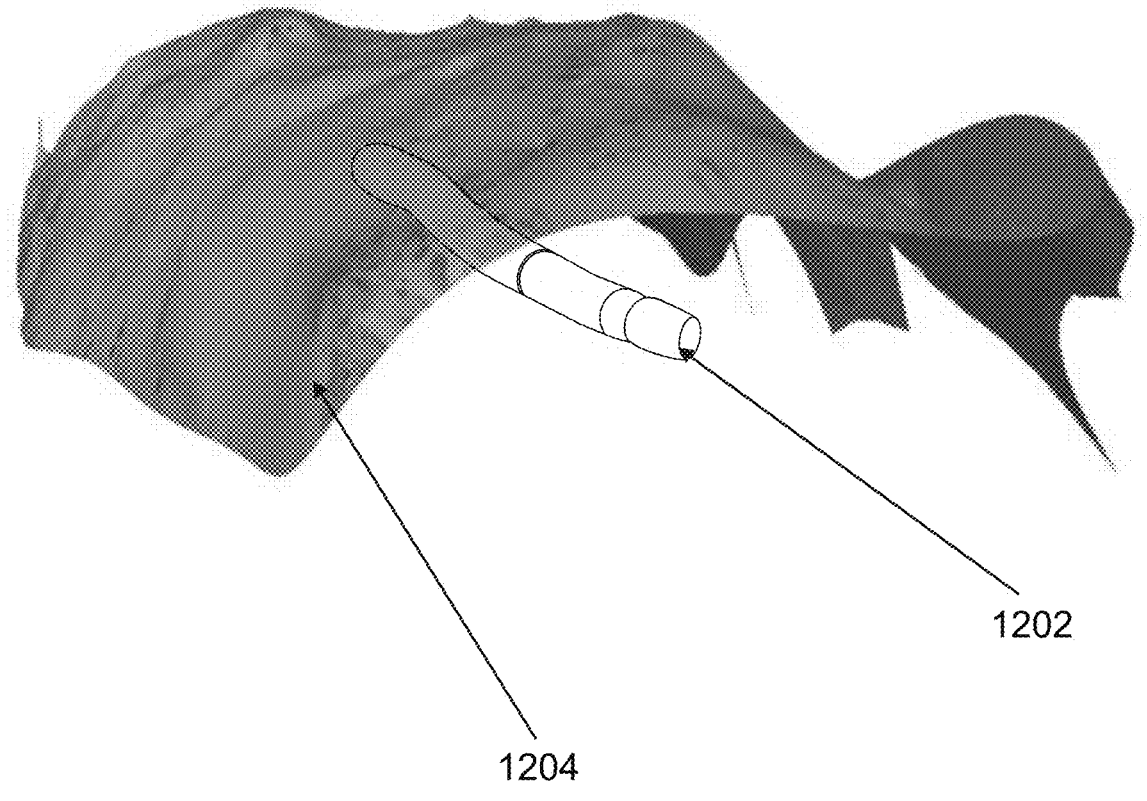
FIG. 12 is a schematic depicting an example 3D image of a brachial artery computed based on camera images depicting a pattern on a surface of an arm of a subject and ultrasound images of the brachial artery, in accordance with some embodiments of the present invention.
Figure 13:
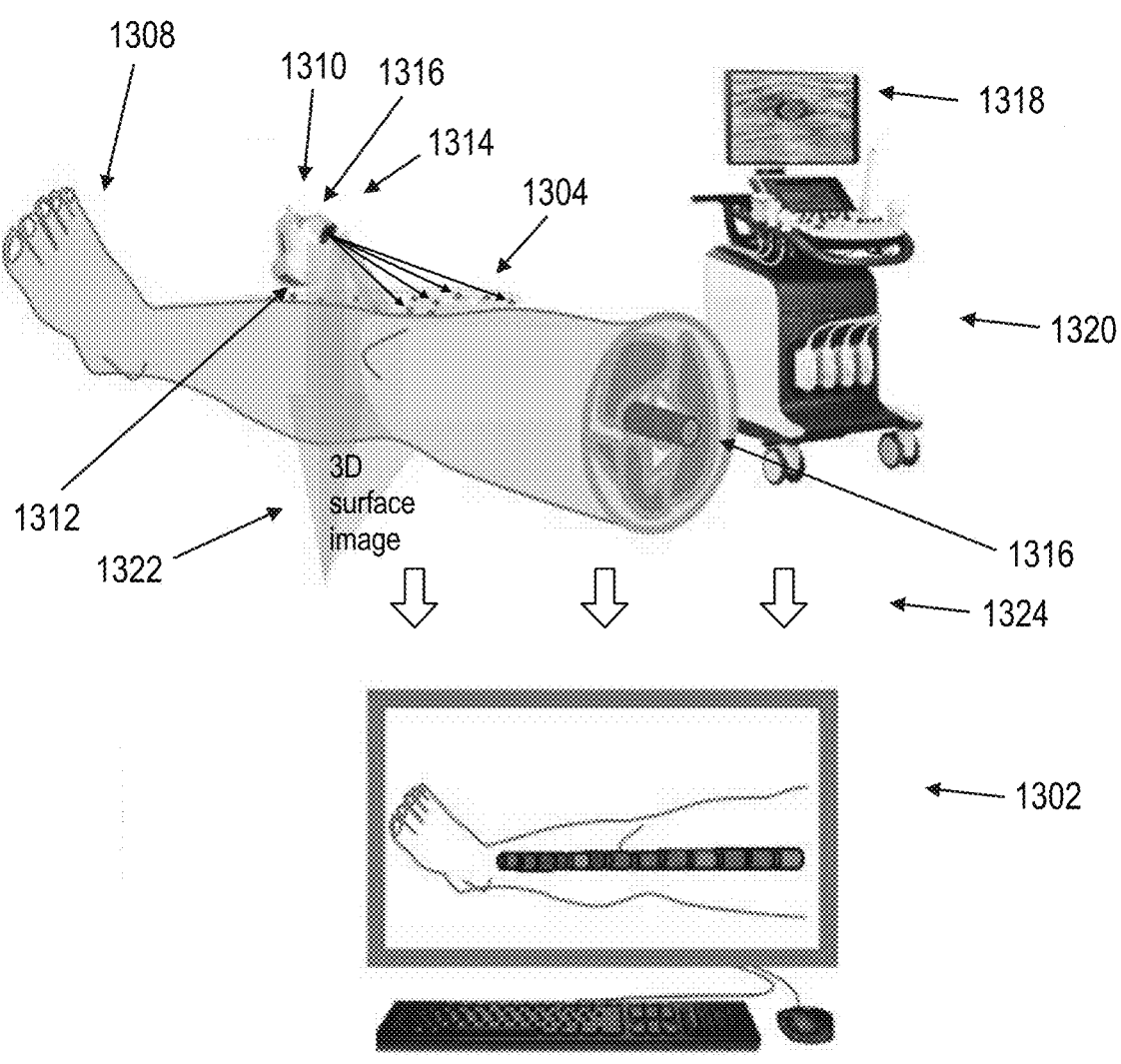
FIG. 13 is a schematic depicting an environment scene of a generation of a 3D image computed from camera images and ultrasound images according to an ultrasonic gel with randomly distributed fiducial objects, in accordance with some embodiments of the present invention.
Figure 14:
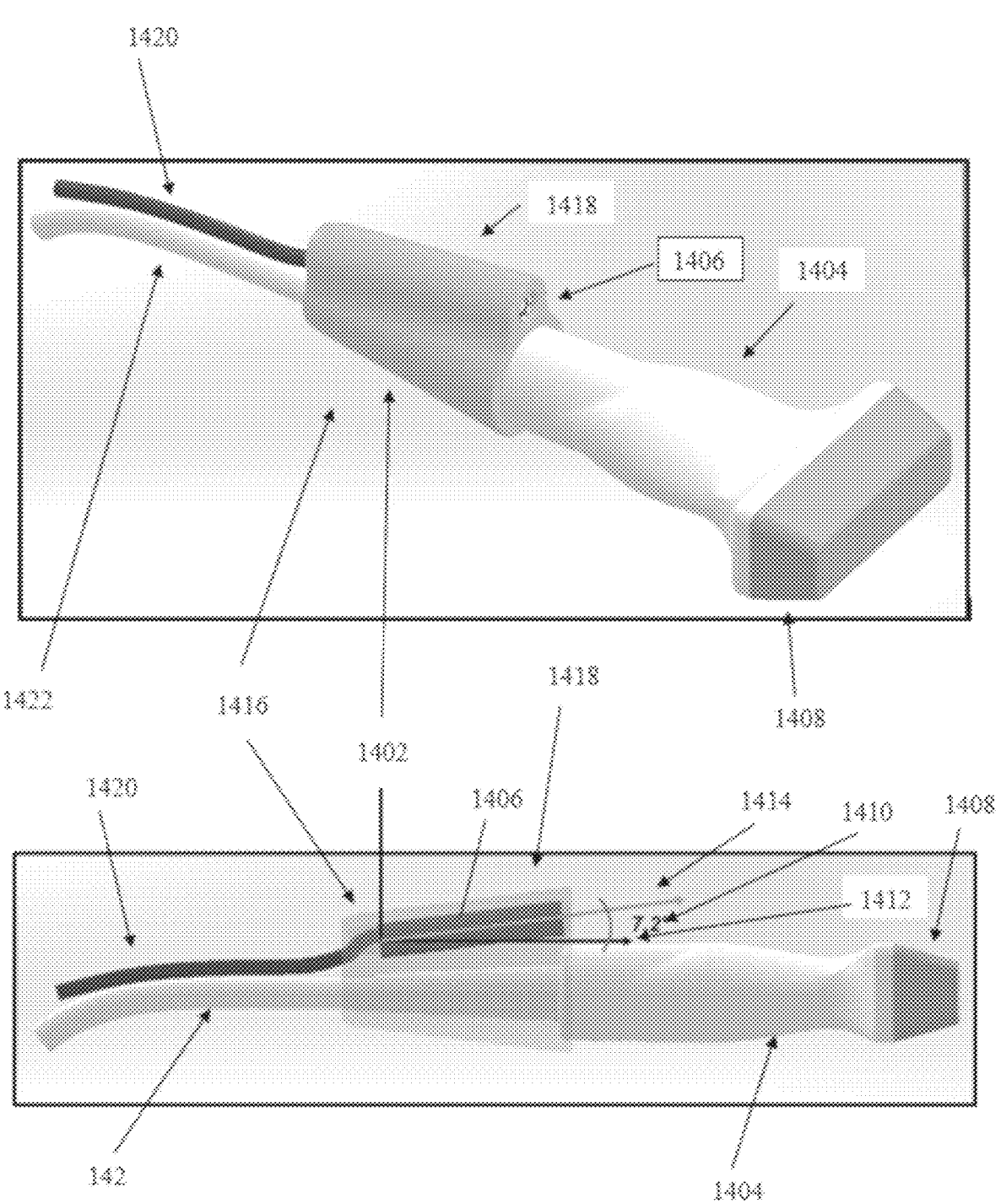
FIG. 14 is a schematic depicting an add-on to an ultrasound probe for capturing camera images by the camera and an ultrasound transducer for capturing ultrasound images used to reconstruct a 3D image, in accordance with some embodiments of the present invention.
Figure 15:
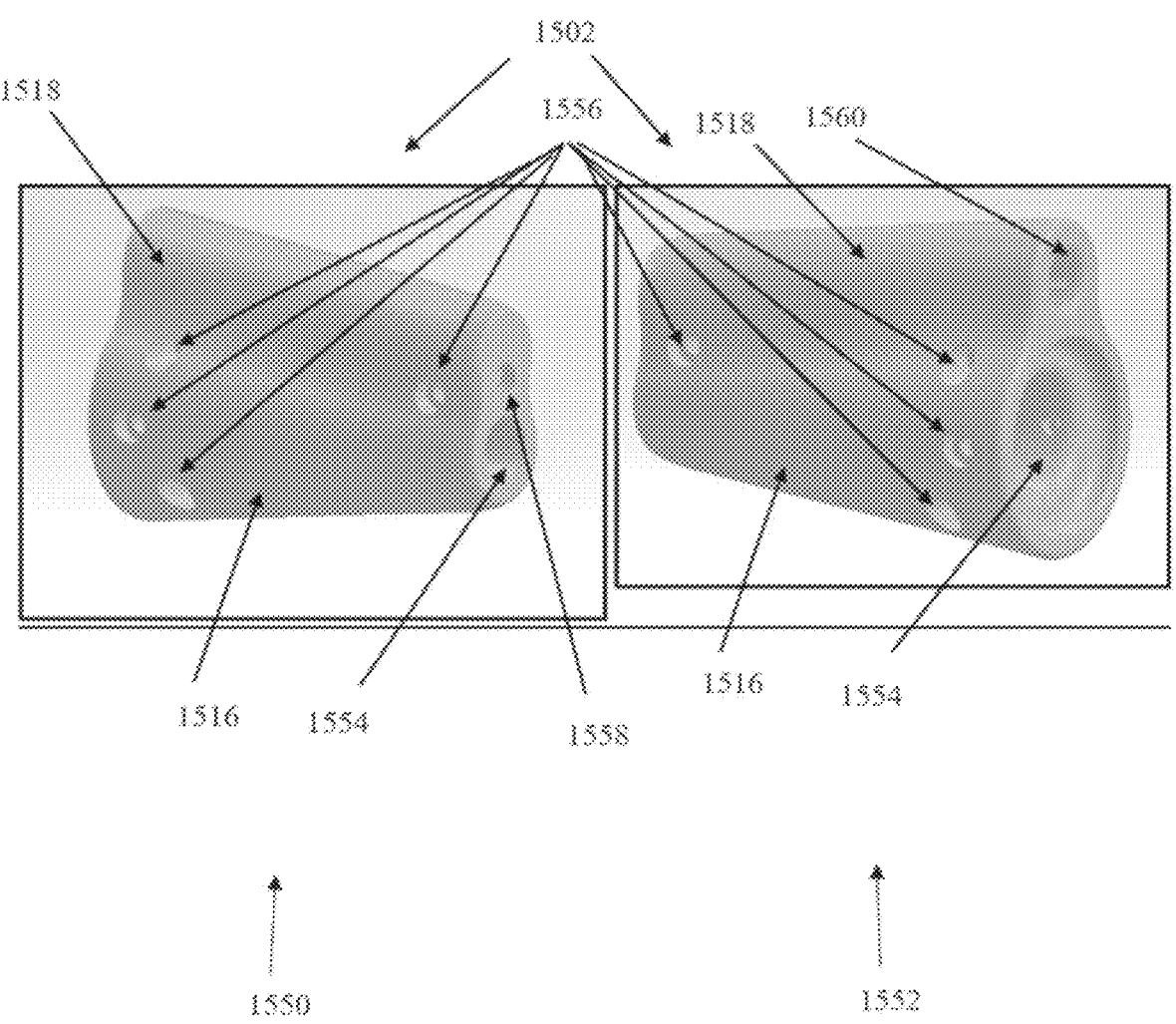
FIG. 15 is a schematic depicting an exemplary add-on to an ultrasound probe, including a connector component sized and shaped for connecting to an ultrasound probe and the camera set at a predefined angle relative to a long axis of the connector component, which corresponds to a long axis of an ultrasound transducer of the probe, in accordance with some embodiments of the present invention.
Figure 16:
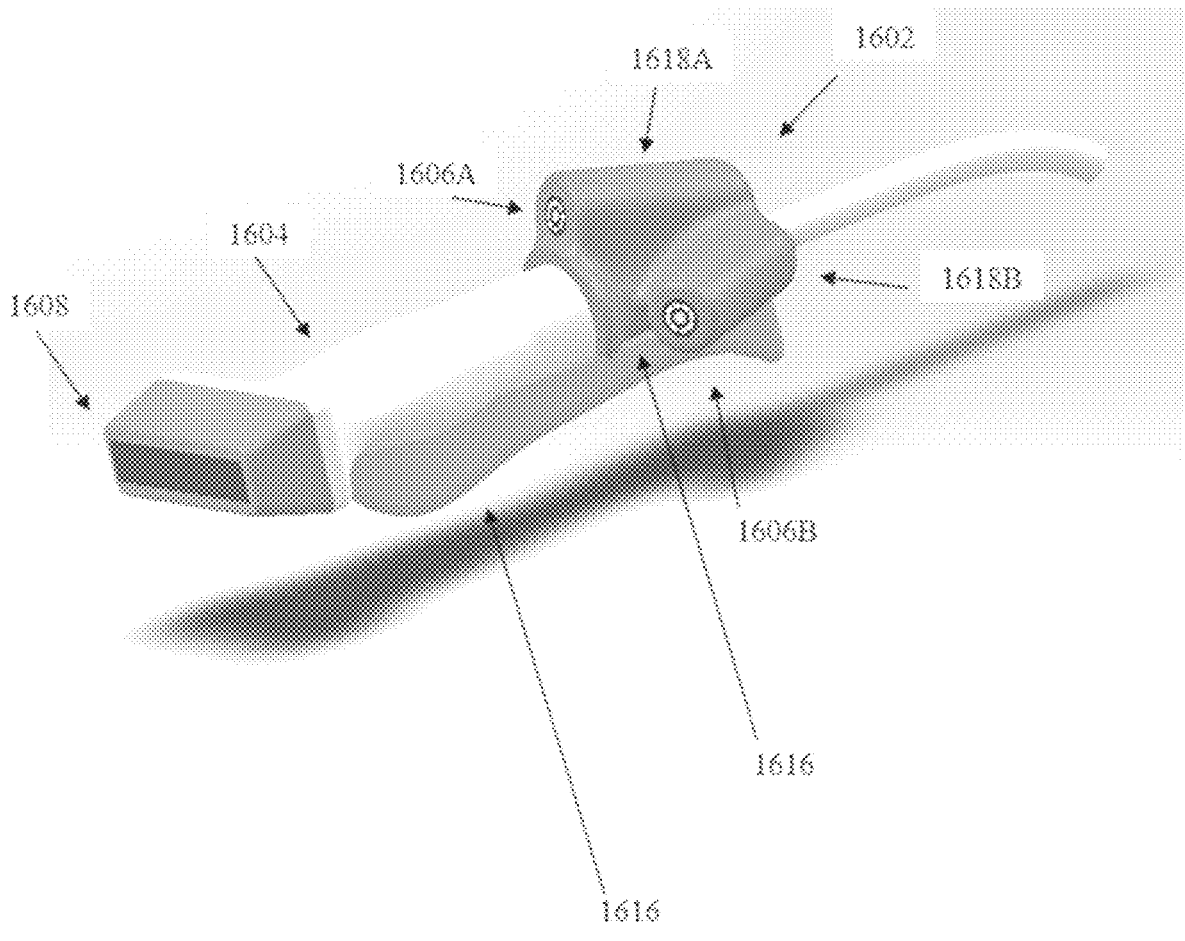
FIG. 16 is a schematic of another exemplary implementation of an add-on to an ultrasound probe, in accordance with some embodiments of the present invention.
Figures 17, 18:
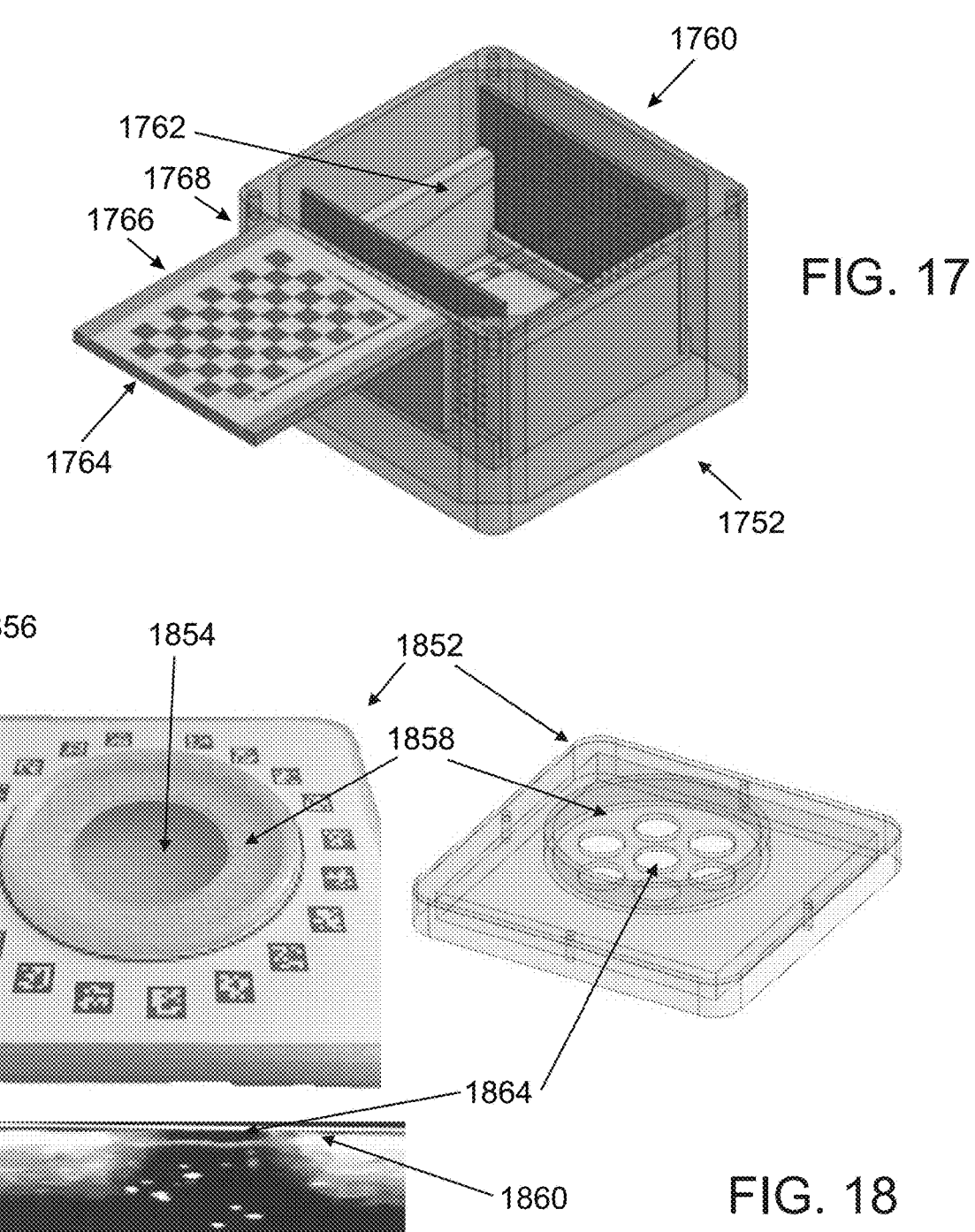
FIG. 17 depicts an exemplary implementation of a calibration device, in accordance with some embodiments of the present invention.
FIG. 18 depicts another exemplary implementation of another calibration device, in accordance with some embodiments of the present invention.
Figure 19:
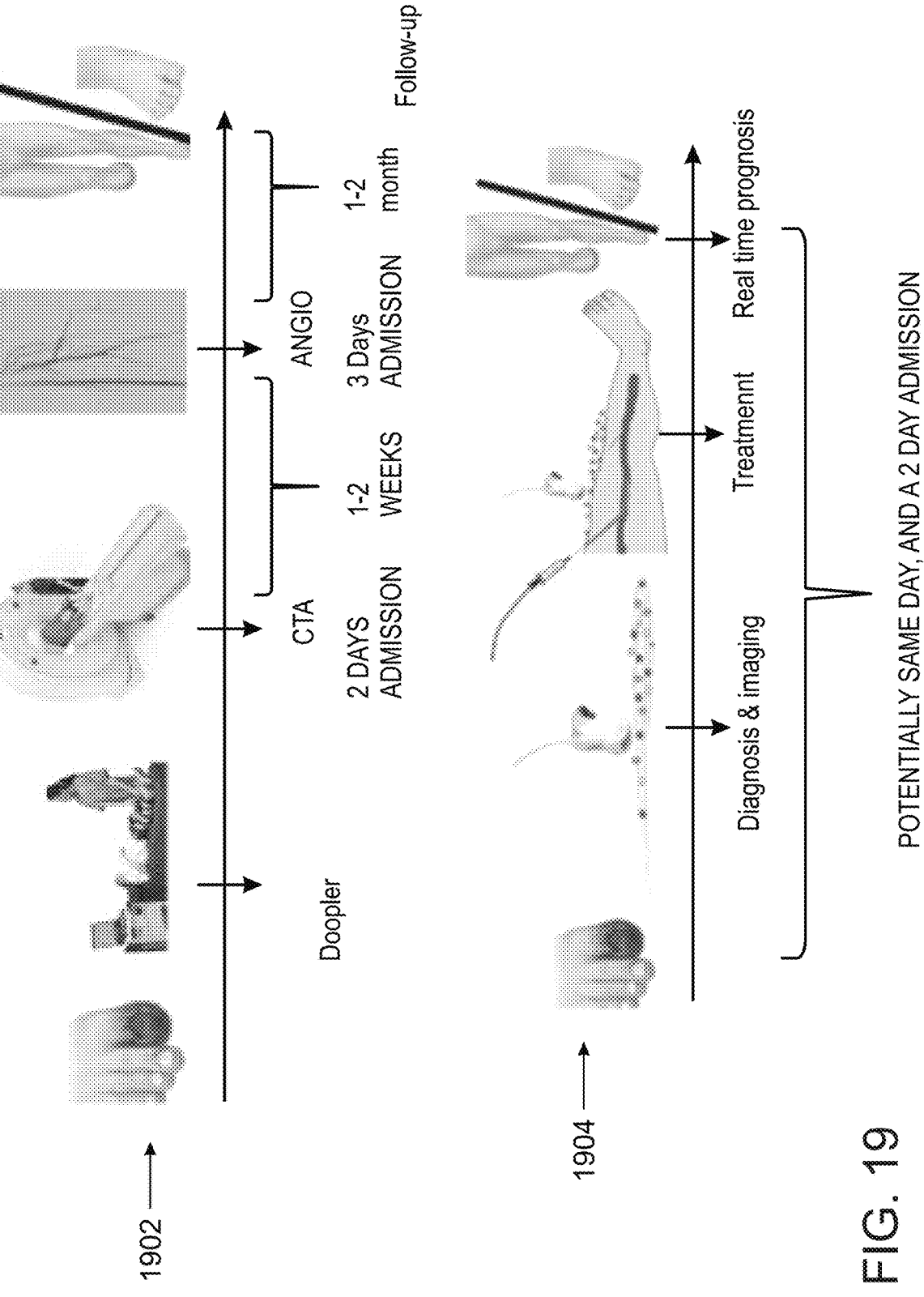
FIG. 19 is a schematic depicting a standard vascular treatment using existing approaches, and a schematic depicting a vascular treatment using the 3D point cloud and/or mesh 3D arteries created from ultrasound and camera images, in accordance with some embodiments of the present invention.
Figure 20:
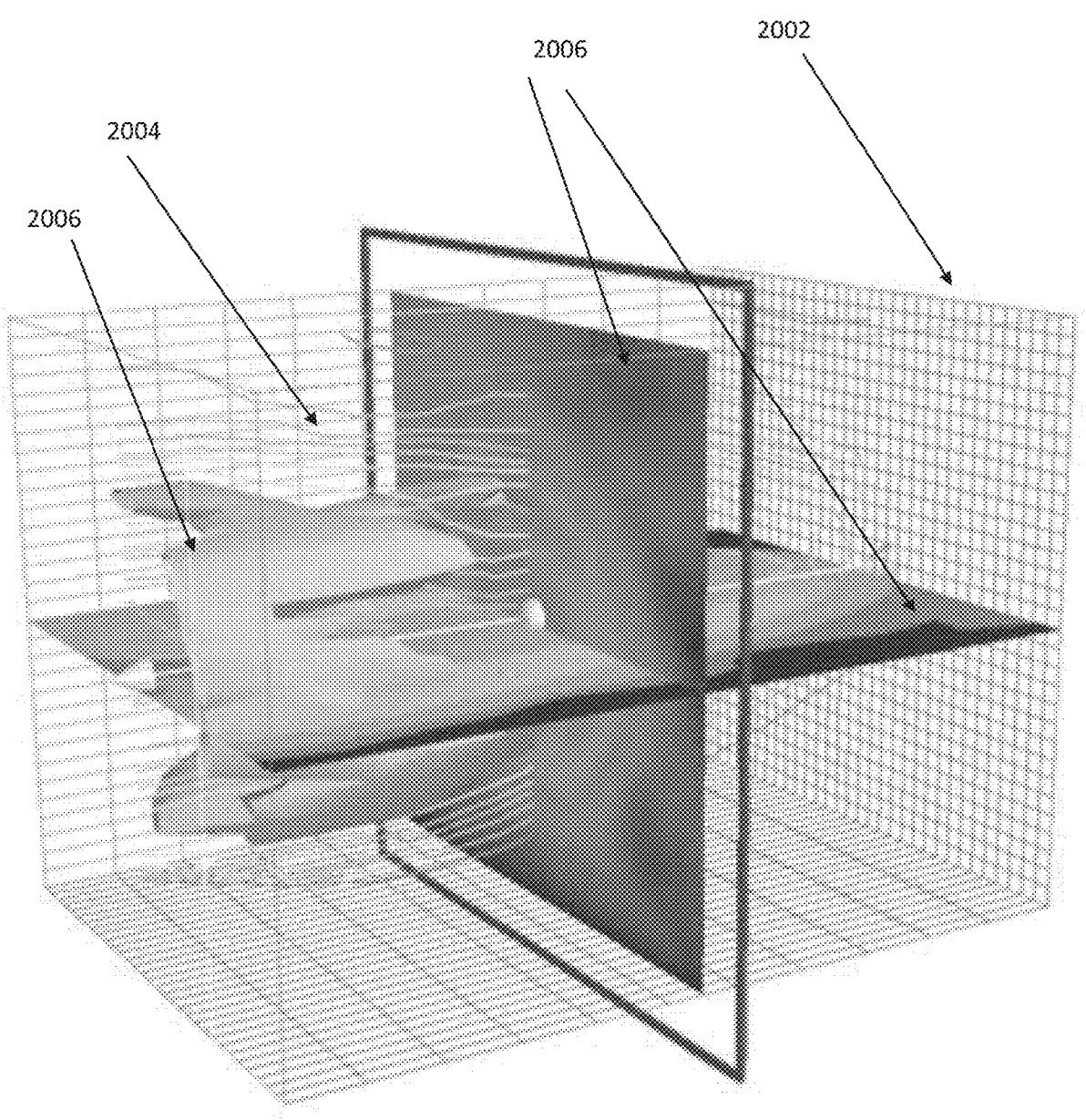
FIG. 20 is a schematic depicting estimation of the blood flow within a blood vessel obtained by an ultrasound transducer at multiple orientations and/or positions as being computed using a known 3D blood vessel model and a computational fluid dynamic simulation, in accordance with some embodiments of the present invention.
Figure 21A:
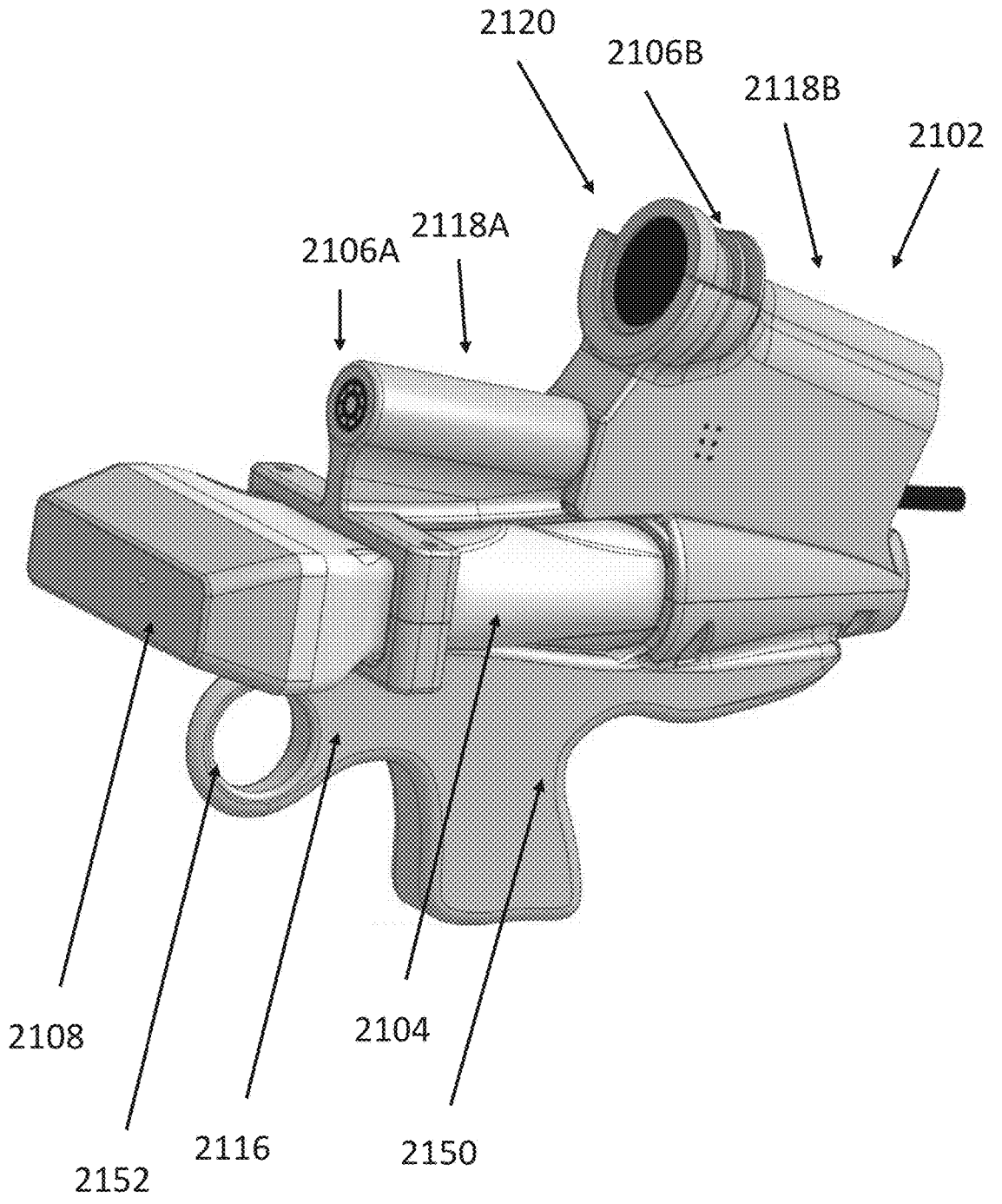
FIGS. 21A-B are schematics of another exemplary implementation of an add-on to an ultrasound probe, in accordance with some embodiments of the present invention.
Figure 21B:
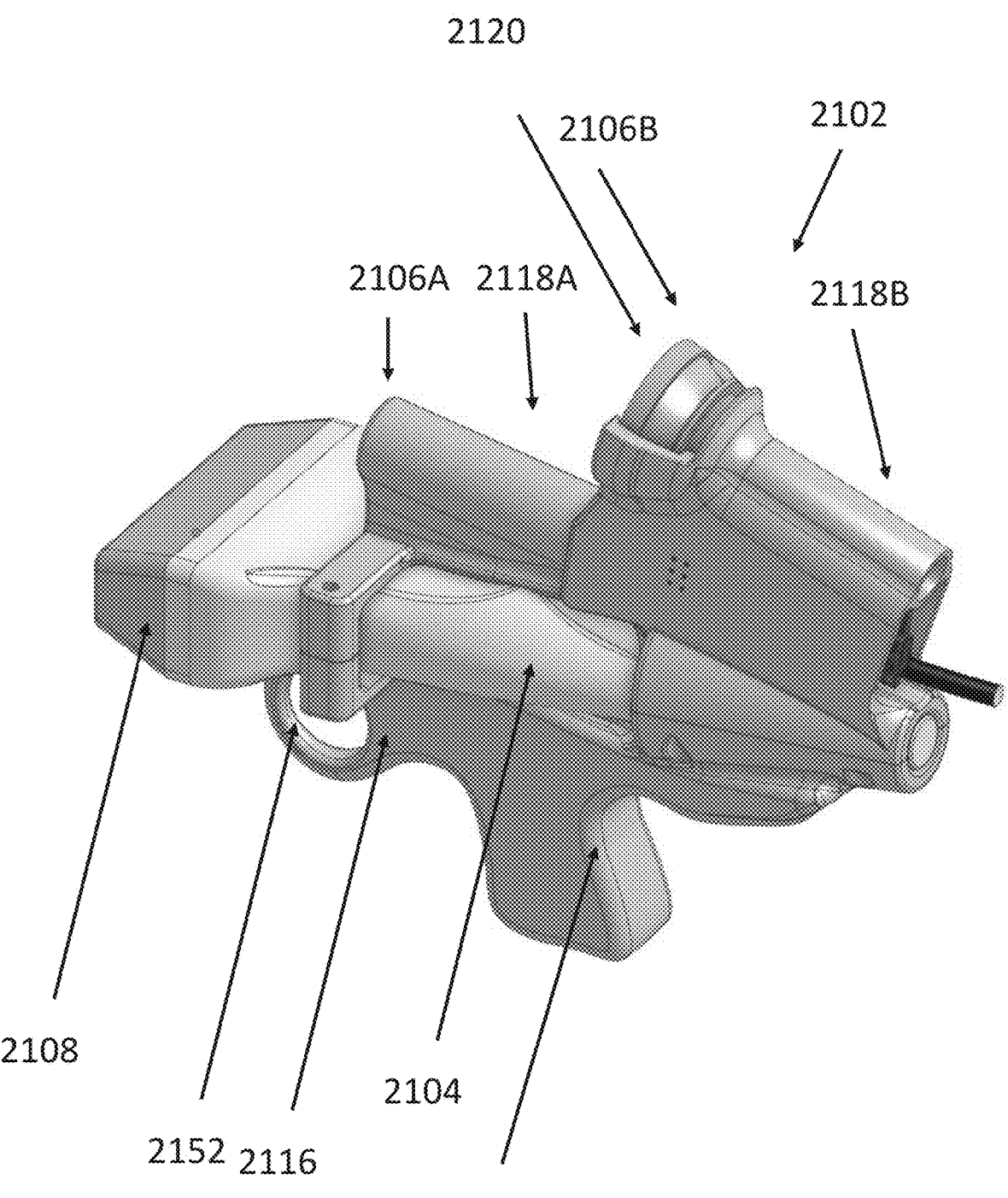

Reference is now made to FIG. 1, which is a block diagram of components of a system 100 for generating 3D images from ultrasound and camera images based on an analysis of relative changes of fiducial objects randomly distributed in a viscous material, in accordance with some embodiments of the present invention. Reference is also made to FIG. 2, which is a flowchart of a method of generating 3D images from ultrasound and camera images based on an analysis of relative changes of fiducial objects randomly distributed in a viscous material, in accordance with some embodiments of the present invention. Reference is also made to FIG. 3, in which is a flowchart of a method of treating a vascular pathology according to 3D images generated from ultrasound and camera images based on an analysis of relative changes of fiducial objects randomly distributed in viscous material, in accordance with some embodiments of the present invention. Reference is also made to FIG. 4, which includes schematics depicting a process of applying an ultrasonic gel with fiducial objects randomly distributed therein for capturing camera images used to reconstruct a 3D image, in accordance with some embodiments of the present invention. Reference is also made to FIG. 5, which is a schematic depicting the camera capturing a camera image of fiducial objects randomly distributed within an ultrasonic gel while an ultrasound transducer of an ultrasound probe captures ultrasonic images through a gel in accordance with some embodiments of the present invention. Reference is also made to FIG. 6, which is a schematic depicting exemplary x,y,z axes of an ultrasound transducer for computing 3D coordinates within a 3D space Vx, Vx, Vz module of a tissue depicted in ultrasound images, in accordance with some embodiments of the present invention. Reference is also made to FIG. 7, which is a schematic depicting a scheme for estimating the actual blood flow within an ultrasound image of a blood vessel obtained by an ultrasound transducer at multiple orientations, in accordance with some embodiments of the present invention. Reference is also made to FIG. 8, which is a schematic depicting reconstruction of a 3D image of an artery depicting a vascular pathology and indicating the velocity of blood flow through the artery, in accordance with some embodiments of the present invention. Reference is also made to FIG. 9, which is a schematic depicting a process of collecting data for one multi-dimensional dataset of one set of 3D coordinates corresponding to one voxel, in accordance with some embodiments of the present invention. Reference is also made to FIG. 10, which is a schematic depicting a representation of a multi-dimensional sparse dataset of a certain voxel, the dataset is represented as colored spheres where the gray values are the acquired gray scale B-mode values of this voxel sparse sampling from various transducer poses, in accordance with some embodiments of the present invention, and another figure depicting several voxel's gray scale sparse distribution values represented as spheres, each voxel is located on an XYZ grid point. Reference is also made to FIG. 11, which is a schematic depicting the reconstruction of a 3D image based on segmentation of clusters of multi-dimensional datasets that include arteries segmented into different tissue types, including a vascular pathology, in accordance with some embodiments of the present invention. Reference is also made to FIG. 12, which is a schematic depicting an example 3D image of a brachial artery computed based on camera images depicting a pattern on a surface of an arm of a subject and ultrasound images of the brachial artery, in accordance with some embodiments of the present invention with the surface of the patient body. Reference is also made to FIG. 13, which is a schematic depicting an environment scene of a generation of a 3D image computed from camera images and ultrasound images according to an ultrasonic gel with randomly distributed fiducial objects, in accordance with some embodiments of the present invention. Reference is also made to FIG. 14, which is a schematic depicting an add-on to an ultrasound probe for capturing camera images by the camera and an ultrasound transducer for capturing ultrasound images used to reconstruct a 3D image, in accordance with some embodiments of the present invention. Reference is also made to FIG. 15, which is a schematic depicting an exemplary add-on to an ultrasound probe, including a connector component sized and shaped for connecting to an ultrasound probe and the camera set at a predefined angle relative to a long axis of the connector component which corresponds to a long axis of an ultrasound transducer of the probe, in accordance with some embodiments of the present invention. Reference is also made to FIG. 16, which is a schematic of another exemplary implementation of an add-on to an ultrasound probe, in accordance with some embodiments of the present invention. Reference is also made to FIG. 17, which is a schematic depicting an exemplary implementation of a calibration device in accordance with some embodiments of the present invention. Reference is also made to FIG. 18, which is a schematic depicting another exemplary implementation of another calibration device, in accordance with some embodiments of the present invention. Reference is also made to FIG. 19, which is a schematic depicting a standard vascular treatment using existing approaches, and a schematic depicting a vascular treatment using the 3D image created from ultrasound and camera images, in accordance with some embodiments of the present invention. Reference is also made to FIG. 20, which is a schematic depicting estimation of the blood flow within a blood vessel obtained by an ultrasound transducer at multiple orientations and/or positions as being computed using a known 3D blood vessel model and a computational fluid dynamic simulation, in accordance with some embodiments of the present invention. Reference is also made to FIGS. 21A-B, which are schematics of another exemplary implementation of an add-on to an ultrasound probe, in accordance with some embodiments of the present invention.

System 100 may implement the acts of the method described with reference to FIGS. 2-21A and 21B, optionally by a hardware processor(s) 102 of a computing device 104 executing code instructions 106A stored in a memory 106.

Computing device 104 may be implemented as, for example, a client terminal, a server, a virtual server, a radiology workstation, an ultrasound workstation, a PACS server, a virtual machine, a computing cloud, a mobile device, a desktop computer, a thin client, a smartphone, a tablet computer, a laptop computer, a wearable computer, a glasses computer, a watch computer, and a ring computer. Computing 104 may include an advanced visualization workstation that sometimes is provided as an add-on to an ultrasound workstation and/or other devices for presenting 3D images that are computed from ultrasound and camera images, as described herein.

Computing device 104 may include locally stored software that performs one or more of the acts described with reference to FIGS. 2-21A and 21B and/or may act as one or more servers, e.g., network server, web server, a computing cloud, virtual server, that provides services, e.g., one or more of the acts described with reference to FIGS. 2-21A and 21B, to one or more client terminals 108, e.g., ultrasound probes, remotely located ultrasound workstations, remote picture archiving and communication system (PACS) server, remote electronic medical record (EMR) server, a computing device that receives ultrasound images and camera images, over a network 110, for example, providing software as a service (SaaS) to the client terminal(s) 108, providing an application for local download to the client terminal(s) 108, as an add-on to a web browser and/or a medical imaging viewer application, and/or providing functions using a remote access session to the client terminals 108, such as through a web browser.

Different architectures based on system 100 may be implemented. In one example, computing device 104 provides centralized services to each one of multiple ultrasound workstations associated with ultrasound transducers 112 of respective ultrasound probes. Each ultrasound transducer 112 is associated with a respective camera 114, which is in a fixed orientation relative to the ultrasound transducer, as described herein. Camera 114 may be installed within an add-on component 254 which is connected to a probe of ultrasound transducer 112, as described herein. Pairs of ultrasound images captured by respective ultrasound transducers(s) 112 and camera images captured by a respective camera(s) 114 are provided to computing device 104, for example, over a network 110, via an API, a local application, and/or transmitted using a suitable transmission protocol, via a data repository, e.g., sever(s) 118 such as PACS, EMR, and/or via client terminal 108. Computing device 104 analyzes the pairs of ultrasound and camera images and computes one or more 3D images, as described herein. The 3D image(s) may be provided to a client terminal(s) 108 and/or server(s) 118 for presentation on a display, storage, and/or further processing. In another example, computing device 104 provides dedicated services to one ultrasound transducer 112 and corresponding camera 114. For example, computing device 104 is integrated with an ultrasound workstation connected to ultrasound transducer 112, e.g., code 106A is installed on the ultrasound workstation that displays ultrasound images captured by the ultrasound transducer, and/or computing device 104 is connected to ultrasound transducer 112 and camera 114, e.g., smartphone running code 106A is connected to ultrasound transducer 112 and camera 114, for example, via a short-range wireless connection, USB cable, and/or other implementations. Ultrasound images captured by ultrasound transducer 112 and camera images captured by camera 114 are processed by locally installed code 106A, and the 3D image(s) is provided for presentation on a display of the ultrasound workstation connected to ultrasound transducer 112 and/or on a display of the locally connected computing device 104 such as the smartphone. Code 106A may provide an additional set of features to the ultrasound workstation connected to ultrasound transducer 112 by dynamically computing the 3D image in real-time, or near real-time, as the ultrasound images and camera images are captured or shortly after the ultrasound images are captured.

In yet another example, ultrasound images captured by ultrasound transducer 112 and camera images captured by camera 114 may be stored in a data repository 122A, for example, a memory and/or storage device of computing device 104, a memory and/or storage device on an ultrasound workstation, e.g., 108, connected to ultrasound transducer 112, an external hard drive connected to a client terminal 108 connected to ultrasound transducer 112 and camera 114, a PACS server, and/or an EMR server, and a cloud storage server, which receive the captured ultrasound images and/or camera images.

Computing device 104 may receive the ultrasound and camera images from ultrasound transducer 112 and/or camera 114 and/or data repository 122A using one or more data interfaces 120, for example, a wire connection, e.g., physical port, a wireless connection, e.g., antenna, a local bus, a port for connection of a data storage device, a network interface card, other physical interface implementations, and/or virtual interfaces (e.g., software interface, virtual private network (VPN) connection, application programming interface (API), software development kit (SDK).

Camera 114 may be, for example, a still camera, a video camera, a CMOS, a visible light-based sensor, for example, a red-green-blue (RGB) sensor such as CCD and/or CMOS sensors, an ultraviolet camera, an infrared camera, a depth RGBD camera and the like.

Hardware processor(s) 102 may be implemented, for example, as a central processing unit(s) (CPU), a graphics processing unit(s) (GPU), field-programmable gate array(s) (FPGA), digital signal processor(s) (DSP), and application-specific integrated circuit(s) (ASIC). Processor(s) 102 may include one or more processors (homogenous or heterogeneous), which may be arranged for parallel processing, as clusters and/or as one or more multi-core processing units.

It is noted that at least some implementations of the systems, apparatus, methods, and/or code instructions described herein are designed to generate the 3D images on processors with relatively few computational resources, for example, a CPU of a smartphone, in comparison to generating the 3D image on high-performance processors such as GPUs. This allows the images to be processed on readily available computational devices, such as a laptop and/or smartphone, rather than requiring the installation of a high-performance processor. Alternatively, at least some implementations of the systems, apparatus, methods, and/or code instructions described herein are designed to generate the 3D images on the high-performance processors.

Memory 106, also referred to herein as a program store and/or data storage device, stores code instruction for execution by a hardware processor(s) 102, for example, a random access memory (RAM), read-only memory (ROM), and/or a storage device, for example, non-volatile memory, magnetic media, semiconductor memory devices, hard drive, removable storage, and optical media, e.g., DVD, CD-ROM. For example, memory 106 may store code 106A that implements one or more acts and/or features of the method described with reference to FIGS. 2-21A and 21B.

Computing device 104 may include a data storage device 122 for storing data, for example, one or more data repositories 122A that document data, for example, received ultrasound and camera images and/or documents the generated 3D images, which may be iteratively updated in response to additional images, multi-dimensional datasets used to compute segmentations, transformation mappings, and/or other data as described herein. Data storage device 122A may be implemented as, for example, a memory, a local hard-drive, a removable storage device, an optical disk, a storage device, and/or as a remote server and/or computing cloud, e.g., accessed over network 110.

System 100 may include an inertial measurement unit, IMU (not shown), which may be installed on add-on to the ultrasound probe 154 for providing measurements indicating pose of ultrasound transducer 112, as described herein.

Computing device 104 may include a network interface 124 for connecting to network 110, for example, one or more of, a network interface card, a wireless interface to connect to a wireless network, a physical interface for connecting to a cable for network connectivity, a virtual interface implemented in software, network communication software providing higher layers of network connectivity, and/or other implementations.

It is noted that data interface 120 and network interface 124 may exist as two independent interfaces, e.g., two network ports, as two virtual interfaces on a common physical interface, e.g., virtual networks on a common network port, and/or integrated into a single interface, e.g., network interface. Computing device 104 may communicate using network 110 or another communication channel, such as through a direct link, e.g., cable, wireless and/or indirect link, e.g., via an intermediary computing device such as a server, and/or via a storage device, with one or more of: Client terminal(s) 108, for example, when computing device 104 acts as a central server providing centralized 3D image generation services, e.g., SaaS, to remote ultrasound workstations 108, acting as client terminals, connected to respective ultrasound transducers 112 and cameras 114, for generating the 3D image from remotely obtained ultrasound and camera images. Server 118, for example, implemented in association with a PACS, which may store ultrasound images and camera images acquired by ultrasound transducer 112 and camera 114 and/or store updated versions of code 106A for upgrade thereof. The 3D image may be reconstructed offline from the image pairs stored on server 118.

Computing device 104 and/or ultrasound transducer 112 and/or camera 114 and/or client terminal(s) 108 and/or server(s) 118 include and/or are in communication with a user interface(s) 126 that includes a mechanism designed for a user to enter data, e.g., patient data, perform a calibration described herein, and/or view data, e.g., reconstructed 3D image. Exemplary user interfaces 126 include, for example, one or more of, a touchscreen, a display, a 3D headset, a keyboard, a mouse, and voice-activated software using speakers and microphones, VR/AR headset.

Optionally, system 100 includes a viscous medium with randomly distributed fiducial objects 150, which is placed within the ultrasonography gel and depicted in images captured by camera 114, for example, an ultrasonic gel with objects (e.g., spheres) suspended therein.

Optionally, system 100 includes an add-on to an ultrasound probe 154, which sets camera 114 in a fixed orientation relative to ultrasound transducer 112, as described herein. Add-on 154 may include a source of illumination, for example, generating visible light, the light of a certain color, ultraviolet light, and/or light for fluorescent activation. The light is selected according to the properties of the fixed orientation, for example, the fiducial objects of the gel, for example, for creating an enhanced visible effect to depict the fiducial objects of the gel in the camera image such as fluorescence of the fiducial objects.

Optionally, system 100 includes a calibration device 152 for calibrating a transformation mapping 122B, as described herein.

At 202, a viscous material, at least a portion of which is fluid, and that includes multiple fiducial objects randomly distributed therein, is provided. The viscous material may be an ultrasonography gel. The ultrasonography gel is designed for application to a surface of a body, e.g., skin of an individual, with which an ultrasound transducer is placed in contact for capturing 2D ultrasound images, e.g., Doppler, B-mode, used to reconstruct 3D images, as described herein.

The fiducial objects are randomly distributed, i.e., within the material, in 3D, and spaced apart by random distances. The fiducial objects are sized and/or have a contrast relative to the viscous material for being depicted by a 2D camera image. The fiducial objects depicted in the camera images are used for the computation of 3D coordinates assigned to pixels of 2D ultrasound images for generating a reconstruction of a 3D ultrasound image depicting an interior of the body and/or the exterior of the scanned body segment.

The fiducial objects may be selected to not interfere with ultrasound energy being transmitted through the ultrasonic gel for capturing ultrasound images, to and/or avoid artifacts created due to the presence of the fiducial objects. For example, the fiducial objects are sized to be small to not interfere with the ultrasound energy being transmitted and/or made out of an acoustic material that transmits ultrasound energy.

The fiducial objects may be non-fixed in specific locations within the ultrasonic gel, such that the fiducial objects flow and/or otherwise change location within the material in response to movement, e.g., shaking, of the material.

Exemplary sizes of the fiducial objects include about 0.5 to 1 millimeter (mm), or about 0.3-1.5 mm, or about 0.5-1.5, or about 0.3-0.7 mm, or other ranges.

Exemplary densities of the fiducial objects include about 10-1000 per milliliter (mL), or about 5-50, or about 25-75, or other ranges.

Exemplary shapes of the fiducial objects include sphere, square, star, snow flake, cube, and any other shape.

The fiducial objects may be colored for contrast with the skin of the individual, such that the fiducial objects are easily discernable by code analyzing camera images captured by a camera. For example, the fiducial objects may be made of fluorescent material, a material that enhanced in response to ultraviolet light (UV), and/or has a bright color such as yellow, green-black, red, blue, or made of a variety of colors and the like Referring now back to FIG. 4, which includes a schematic of an ultrasonic gel 404 with fiducial objects randomly distributed therein 406 for capturing image cameras used to reconstruct a 3D image. Ultrasonic gel 404 may be applied, for example, from a container, e.g., by squeezing a plastic bottle. Ultrasonic gel 404 may be applied in a standard way, spread over the skin of a subject above tissue being imaged and its surrounding. Optionally, ultrasonic gel 404 is spread over a wider area of the body for generating a 3D image reconstruction of a larger area tissue region than that depicted by individual 2D ultrasound images, for example, an organ, e.g., liver, kidney, and/or vascular tree and/or tree. Optionally, ultrasonic gel 404 is spread over a region large enough to be captured in the camera images. The ultrasound transducer is moved over ultrasonic gel 404 to capture ultrasonic images, while a camera, e.g., in an add-on connected to the ultrasound transducer, captures camera images of fiducial objects randomly distributed 406 within gel 404, where the camera images are used to reconstruct 3D images, as described herein.

Randomly distributed fiducial objects 406 provide multiple features throughout the camera images for computing the 3D coordinates assigned to 2D pixels for obtaining 3D voxels to reconstruct the 3D image. The multiple features spread out over the camera image may increase the accuracy of the location of the 3D voxels.

Fiducial objects 406 have a size and/or color feature selected for being depicted in the camera image captured by the camera when the ultrasonic gel 406 is spread over the surface of the skin of the subject. Fiducial objects 406 may have a small size selected and/or are made out of an acoustic material selected for not being depicted in the ultrasound image(s) captured by the ultrasound transducer via the ultrasonic gel 404. The size of fiducial objects 406 may be, for example, about 0.5 to 3 millimeter(s) (mm), or about 0.5-1 mm, or about 1-2 mm, or other ranges. Optionally, gel 404 is clear, while the color feature is non-clear, optionally of one or more different colors, for example, yellow, red, green, black, and blue. Optionally, fiducial objects 406 are made of a material that provides the color feature of being enhanced in response to ultraviolet light and/or made of fluorescent material. Fiducial objects 406 may be of different shapes, for example, sphere-shaped, squares, triangles, diamonds, or other shapes. A density of fiducial objects 406 within ultrasonic gel 404 may be about 10-1000 per milliliter (mL), or about 5-50, or about 25-75, or about 10-100, or about 100-500, or about 300-700, or other ranges.

Referring now back to FIG. 2, at 204, ultrasound images depicting internal body tissue captured by an ultrasound transducer are obtained. The ultrasound images depict a common region of a body segment, for example, a blood vessel, e.g., femoral artery, carotid artery, aorta, or other internal body tissues, e.g., kidney, liver, gallbladder, spleen, thyroid.

The ultrasound images may include Doppler 2D mode images and/or B-mode images or other 2D/3D modes.

The internal body tissue may include moving fluid, for example, blood vessels. For the case of blood vessels, the ultrasound images may further include Doppler data, also referred to herein as Doppler images. The ultrasound images include a region of the blood vessel depicting blood flowing therein. The Doppler ultrasound images further include a measurement of blood flow in a region of the blood vessel. The blood flow measurement may be an instantaneous blood flow measurement, e.g., maximal velocity, and/or a pattern of change of blood flow, e.g., velocity over one or more cardiac cycles.

Optionally, Doppler ultrasound images and B-mode ultrasound images are alternated, for example, when blood vessels are being images.

At 206, 2D camera images captured by a camera are obtained. The camera image is optionally visible light images captured by a standard video camera and/or still camera. The camera images depict a feature pattern, optionally the fiducial objects within the ultrasonic gel or other viscous material. It is noted that other feature patterns may be used, for example, a temporary tattoo placed on the skin and/or features of the skin itself, e.g., hair, birthmarks, wrinkles.

The camera is located at a known fixed pose relative to the ultrasound transducer. Optionally, the camera is installed as an add-on to the ultrasound transducer, designed to be set at the fixed pose.

Optionally, the camera images and the ultrasound images are captured simultaneously or near-simultaneously.

Optionally, the camera images and the ultrasound images are captured as pairs, i.e., synchronized and/or at matching video frame rates. Alternatively, the camera images and ultrasound images are captured independently, for example, at different video frame rates.

Referring now back to FIG. 5, which is a schematic depicting a camera 502 capturing a camera image, depicted by a field of view 504, of fiducial objects 506 randomly distributed within an ultrasonic gel 512, or other viscous material, while an ultrasound transducer 508 of an ultrasound probe 510 captures ultrasonic images through gel. Camera images depicting the fiducial objects 506 randomly distributed within an ultrasonic gel, and the ultrasound images are used for computing 3D voxels to reconstruct a 3D image, as described herein. Camera 502 may be located in an add-on 514 connected to ultrasound probe 510, where the add-on 512 is set to fix an angle of camera 502, e.g., angle of view for capturing the camera images, relative to the ultrasound transducer 508, e.g., to view for capturing the ultrasound images, as described herein.

Referring now back to FIG. 2, at 208, 3D voxels having 3D coordinates within a world coordinate system are computed. The world coordinate system represents the body segment of the individual being imaged and defines real-world distances and/or real-world locations, i.e., without distortion. The world coordinate system may be a 3D Euclidean space within which the body segment is located, isotopically scaled to real-world distances, e.g., 1:1 or other linear scales, and/or is in a non-deformed space. The 3D voxels are computed by assigning 3D coordinates to pixels of the 2D ultrasound images and/or to the Doppler images using an external reference of the ultrasound transducer pose that captured the ultrasound images. The pose of the ultrasound transducer is computed by analyzing relative changes in locations of the fiducial objects within sequential 2D camera images.

3D coordinates may be computed for pixels of the Ultrasound and/or Doppler images by computing a pose of the camera in a camera coordinate system relative to the world coordinate system. The actual scale of the structure and motion in world units may be calculated by additional information, such as the size of an object in the 2D camera image like the diameter of the spheres embedded within the ultrasonography gel, or by adding information from another sensor like inertial measurement unit, or by another camera. The pose of the camera may be computed by analyzing relative changes in locations of the fiducial objects within sequential 2D camera images, for example, computed using optical flow, structure from motion, visual odometry, or by visual simultaneous localization and mapping and the like. A calibrated mapping, e.g., transformation matrix, may be used for mapping pixels of the ultrasound and/or Doppler images represented in an ultrasound coordinate system of the ultrasound transducer to the camera coordinate system. The mapping may be based on a pre-calibrated relationship between the pose of the camera and the pose of the ultrasound transducer. The pixels of the ultrasound and/or Doppler images represented in the camera coordinate system are mapped to the 3D coordinates within the world coordinate system. The voxels are created by assigning the pixel intensity values of the pixels of the ultrasound and/or Doppler images to the corresponding 3D coordinates within the world coordinate system.

Reference is now made to FIG. 6, which is a schematic depicting exemplary x,y,z axes 606 of an ultrasound transducer 602 for computing 3D coordinates within a 3D space Vx, Vx, Vz module 608 of a tissue 604, i.e., volume of interest, depicted in ultrasound images. The orientation of ultrasound transducer 602 defined by axes 606 and/or computation of 3D voxels for tissue 604 within 3D space 608 are computed based on camera images captured by a camera 610 connected to ultrasound probe 612 of ultrasound transducer 602, for example, housed within an add-on component 614, as described herein.

Referring now back to FIG. 2, three types of 3D images, which may be included in a single 3D image and/or presented as different 3D images and/or as different overlays of the same 3D images, may be computed.

Features 210-214 are for computing a 3D image depicting blood flow in the blood vessel.

Features 216-222 are for segmenting the 3D image.

Features 224-226 are for computing a 3D image depicting body surfaces.

At 210, an (e.g., initial) estimated blood flow is computed and/or obtained for multiple locations within the blood vessel. Optionally, the (e.g., initial) estimated blood low is computed and/or obtained throughout the blood vessel, for example, along the length and/or diameter of the blood vessel.

Many or all of the (e.g., initial) estimated blood flow values for the different locations in the blood vessel are measured at a non-90 degree angle between a long axis of the ultrasound transducer (e.g., along with the ultrasound probe) and a vector denoting the direction of blood flow in the blood vessel. Measurements made at the non-90 degree angle are incorrect values since Doppler measured blood flow is designed to be made at non 90 degrees.

At 212, the blood flow values measured at non-90 degree angles are corrected to account for the actual blood flow velocity vector along within the artery.

Different approaches may be used for correcting the measured blood flow to obtain the actual blood flow. The first, second, and third approaches described below are for computing flow, e.g., meters/second. The fourth approach described below is for volumetric flow, e.g., ml/second. A fifth approach described below is for full blood flow velocity vector field estimation:

In a first approach, an elliptical-shaped boundary of the blood vessel is identified. The elliptical shape may be identified, for example, by a neural network trained on a training dataset of ultrasound images labeled with elliptical-shaped boundaries, by matching to a template of elliptical-shaped boundaries, by applying a filter to the images to contrast edges and using an edge shaped process to find the boundaries and computing the shape of the boundary, and/or other image processing approaches. A transformation of the elliptical shape to a circle is computed. The transformation is applied to the measurement of blood flow to obtain the estimated actual blood flow.

In a second approach, an estimate of a longitudinal axis of the blood vessel is computed based on an aggregation of multiple 3D points obtained from respective planes of acquisition of each of multiple Doppler ultrasound images. For each respective current Doppler image, the current tangent to the longitudinal axis of the blood vessel is computed by finding the local principal component analysis (PCA). The measured blood flow is corrected based on a projection by an angle between measured blood flow and a normal to the respective plane of acquisition which is along the tangent.

In a third approach, for each respective 3D voxel, multiple initially estimated blood flows and a corresponding normal to a plane of the ultrasound transducer at which a respective Doppler US image used to compute the respective initial estimated blood flow is captured are recorded. The real blood flow in each voxel is estimated by minimizing a projection error between the recorded blood flow velocity vector and the assumed flow velocity vector.

In a fourth approach, an initial volumetric flow within the blood vessel on a sagittal view is obtained at a specific location for multiple cardiac cycles. The initial volumetric flow may be computed using standard approaches, e.g., Doppler, but is obtained for a non-90 degree angle. An initial average volumetric flow is computed by averaging the initial volumetric flow over the cardiac cycles. A gamma value denoting a real number in a range of −1 to 1 is computed to correct the initial average volumetric flow to obtain actual volumetric flow. The estimated actual blood flow may be obtained by correcting initial measured blood flow, for example, based on the first, second, and/or third approaches described above. A cosine angle may be computed from an inverse of the gamma value. The initial average volumetric flow is corrected to obtain the actual volumetric flow using the cosine angle and the dot product between the estimated and the actual blood flow.

In the fifth approach, also depicted with respect to FIG. 20, a 3D model of the actual blood vessel is computed based B-Mode segmentation, and a computational fluid dynamics model is employed together with aggregation of multiple 3D points obtained from respective planes of acquisition of each of multiple Doppler ultrasound images as the boundary condition for generating a full blood flow velocity vector field at each virtual point within the artery.

Referring now back to FIG. 7, a schematic depicting correction of flow, e.g., velocity, speed, and blood 702 within an ultrasound image of a blood vessel 704 obtained by an ultrasound transducer 706 at multiple orientations 708, is presented. Graphs 710 depict measurement of blood flow 704 obtained at different orientations 708 of transducer 706, which are corrected as described herein.

Referring now back to FIG. 2, at 214, a 3D image is reconstructed in the world coordinate system by aggregating the 3D voxels, where multiple 3D voxels each include a respective estimated, i.e., corrected, blood flow. The 3D image depicts an anatomical image of the blood vessel and depicts blood flow at multiple locations within the blood vessel.

Optionally, the 3D image is reconstructed from 3D voxels computed from B-mode ultrasound images, and the indication of estimated blood flow associated with each 3D voxel is computed from the Doppler data.

Optionally, 3D voxels of the reconstructed 3D image are visually coded according to the corresponding blood flow, for example, color-coded. For example, blood flow within a range indicating slow flow is colored one color, e.g., blue, and blood flow within another range indicating fast flow is colored another color, e.g., red, and the like. Alternatively, or additionally, pixels of the Doppler ultrasound images are visual, e.g., color, coded denoting blood flow. The colored pixels may be segmented. The 3D image may be reconstructed from 3D voxels corresponding to the segmented color pixels.

Optionally, the respective estimated blood flow of the 3D voxels is selected as maximal values over an imaging time interval during which the Doppler ultrasound images depicting the region within the blood vessel corresponding to the 3D voxels are captured. Alternatively, or additionally, a plurality of Doppler ultrasound images used to compute the 3D voxels are captured over an imaging time interval depicting variation in blood flow, which can be plotted as a linked graph, and wherein the reconstructed 3D image includes, for the 3D voxels, a respective indication of variation in blood flow over the imaging time interval. The reconstructed 3D image may be presented as a video over the imaging time interval by varying the blood flow values corresponding to the 3D voxels over the imaging time interval according to the captured correlation.

The following is exemplary pseudocode for generating a 3D image that depicts blood flow speed at multiple locations of a blood vessel:

```
3D reconstruction of the patient's body:
USInit+transucerCamInit
Record synchronized Videos
For every frame in transducer camera
    if frame is good then add to database
For every frame in database
    featureExtraction
    ImageMatching
    FeatureMatching
    StructureFromMotion
    PrepareDenseScence
    ComputeDepthMapFilter
    Meshing
    MeshingFiltering
    Texturing
end
From StructureFromMotion extract Camera Poses
For each cameraPose in Poses
    extractSegmentedPixels based on color and maximum value
computeHomogenousTransform from the transducer
corrdinate system to world system
end
For each colored point in PointCloud
    CorrectVelocityMeasurement
End
Display 4D data
```

Referring now back to FIG. 8, a schematic depicting the reconstruction of a 3D image 802 of artery 804 depicting a vascular pathology 806 (e.g., stenosis) and indicating the velocity of blood flow 812 and 814 through artery 804, is provided. An ultrasound probe 808, which includes an ultrasound transducer and camera, as described herein, is maneuvered across a surface of a leg, above artery 804, including lesion 806, for example, using a scanning motion at different orientations. The blood flow measured at different locations at different orientations is corrected, as described herein. Multiple standard ultrasound images 810 are captured, including optional Doppler data, along with camera images of a pattern, e.g., fiducial objects in an ultrasonic gel applied across the surface of the leg. 3D reconstruction 802 of artery 804 is computed from the ultrasound images, the camera images, and optional Doppler data. 3D reconstruction 802 depicts a portion 812 corresponding to vascular pathology 806, identified by abnormally fast blood velocity and/or abnormal indication, e.g., stenosis, calcification, high blood velocity, stent, and depicts other portions 814, which are normal parts of the artery, identified by normal blood velocity and/or normal shape.

Referring now back to FIG. 2, at 216, a 3D image is reconstructed from the 3D voxels.

At 218, a multi-dimensional dataset is computed for each 3D voxel of the 3D image. Each multi-dimensional dataset includes a mapping between the respective pose of the ultrasound transducer during capture of each respective ultrasound image depicting the 3D coordinates in the body corresponding to the 3D voxel and intensity values obtained at the 3D coordinates for each respective ultrasound image acquired from various transducer poses. The pose of the ultrasound transducer may be represented, for example, by six values denoting 6 degrees of freedom. For example, for 3D voxel at coordinates (x,y,z): (a1, b1, c1, d1, e1, f1)→intensity Q1, (a2, b2, c2, d2, c2, f2)→intensity Q2, and (a3, b3,c3, d3, e3, f3)→intensity Q3.

Referring now back to FIG. 9, a schematic depicting a process of collecting data for a certain multi-dimensional dataset of a certain set of 3D coordinates corresponding to a certain voxel. Different pixel intensity values are collected for the same tissue region 902 by varying the pose of the ultrasound transducer, visually depicted as multiple ultrasonic imaging planes 904, is provided.

Referring now back to FIG. 10, a schematic depicting a representation of a multi-dimensional (optionally sparse) dataset 1002 of a certain voxel where the acquired grayscale values distribution has represented a sphere, is provided. A respective location within the sphere denotes a 3D pose and/or orientation of the ultrasound transducer during the capture of the respective 3D voxel corresponding to the respective multi-dimensional (optionally sparse) dataset. A respective intensity value at the respective location of the sphere denotes a pixel intensity value of a 2D pixel of a 2D ultrasound image corresponding to 3D coordinates of the 3D voxel computed from the 2D pixel at the 3D pose and/or orientation of the ultrasound transducer corresponding to the respective location, or/and estimated by Filling in-between values can be done by interpolation, or by a voting scheme which draws additional information from K-neighbors. For example, the intensity at location 1004, e.g., visually depicted as dark, is different from the intensity at location 1006, indicating differences in distributions of the 3D pose and/or orientation during the capture of the certain 3D voxel, which is the same tissue but has a different grayscale 'fingerprint' identification. Schematic 1008 represents multiple multi-dimensional sparse datasets, one marked 1010 for clarity, within a real world coordinate system, where each multi-dimensional dataset corresponds to one voxel used to create the 3D image. Multi-dimensional datasets may be clustered and segmented, as described herein.

Referring now back to FIG. 2, at 220, the 3D voxels are clustered into clusters according to a distribution of the multi-dimensional sparse datasets of the 3D voxels.

Clustering may be performed based on manifold learning for finding a subspace for better clustering the data.

The clustering may be performed by clustering voxels according to similar patterns of changes in captured ultrasound data for different angles and/or distances of locations corresponding to the respective voxels relative to an ultrasound transducer. Voxels in each respective cluster indicate a respective tissue type that creates a respective similar pattern of change in captured ultrasound data for different angles and/or distances relative to the ultrasound transducer.

Clustering may be based on unsupervised learning approaches, for example, by minimizing a statistical distance between voxels in each cluster and maximizing the statistical distance between clusters. The statistical distance may be based on an encoding, for example, indicating patterns of changes in captured ultrasound data for different angles and/or distances of locations corresponding to the respective voxel relative to an ultrasound transducer.

Reference is now made to FIG. 11, a schematic depicting the reconstruction of a 3D image 1102 based on segmentation of clusters of multi-dimensional datasets, which includes artery 1104 segmented into different tissue types including a vascular pathology 1106, e.g., stenosis, calcification, a stent, is provided. An ultrasound probe 1108, which includes an ultrasound transducer and camera, as described herein, is repeatedly maneuvered at the skin above lesion 1106 at multiple different orientations. Data collected for the region, including lesion 1106, including standard ultrasound images, optional Doppler data, and camera images of a pattern, e.g., fiducial objects in an ultrasonic gel applied across the surface of the leg), are aggregated to generated a higher resolution 3D reconstruction 1112 of reconstructed image 1102 and/or higher resolution ultrasound image 1110, as described herein. The pose of the ultrasound transducer and corresponding pixel intensities are included in respective multi-dimensional datasets, where each multi-dimensional dataset is for each 3D coordinates corresponding to a single voxel used to generate the 3D image. The higher resolution ultrasound image 1110 may be segmented, by clustering the voxels according to similar multi-dimensional sparse datasets, i.e., according to similar distributions in pixel intensity values of ultrasound images during different orientations of the ultrasound transducer. Each segmented region may correspond to a respective tissue type. 3D reconstruction 1102 depicts a higher resolution portion 1112, which is segmented to include vascular pathology 1106, which may depict abnormal blood velocity and/or abnormal shape, e.g., stenosis, calcification, high blood velocity, a stent.

Referring now back to FIG. 2, at 222, the 3D image is segmented according to subsets of 3D voxel members of each cluster. Each segmentation includes the 3D voxels, which are members of a respective cluster. Each segmentation may represent a certain tissue type.

The resulting clusters are the segmented regions. The manifold and the clustering may be designed to consider the spatial and/or temporal distribution of each voxel to find clusters of voxels, optionally in a non-supervised manner, groups within where each group is assigned as a respective tissue type. This process may improve the resolution of the ultrasound machine and/or extract geometrical shapes and/or features of relevant issues.

The following is exemplary pseudocode for computing the segmentation:

```
For each pixel in the image
    Compute Pixel Location In Point Cloud
    Store Gray Scale Value for each voxel and colored
        Doppler with the transducer orientation and position
        as a 3D vector
    end
    Perform Voxelization
    Group voxels based on Manifold Learning and/or other
``` clustering where voxels with similar grayscale values belong to the same group than those in other groups, this includes calculating group assignment based on distances between members, the distance may be calculated based on some computed manifold or latent representation, density threshold, or setting up a priori the number of expected clusters, and/or formulated as a multi-objective optimization problem. Various approaches for clustering may be employed, such as: connectivity-based clustering, centroid-based clustering, distribution-based clustering, density-based clustering, grid-based clustering or the like.

At 224, 3D coordinates are computed for pixels of the 2D camera images depicting the surface of the body segment, optionally the skin. The whole 2D camera image may depict the surface. When some of the camera images depict the surface, and some do not depict the surface, e.g., depicts background around the body portion, the surface may be segmented. The 3D coordinates are computed based on the analysis of relative changes in locations of the fiducial objects within sequential 2D camera images, optionally the analysis performed for computing 3D coordinates for the ultrasound images.

The 3D coordinates assigned to pixels of the 2D camera images and to pixels of the 2D ultrasound images are within a common coordinate system. Voxels are defined within the 3D coordinate system by assigning the 3D coordinates to the pixels of the 2D camera and ultrasound images.

Optionally, the 2D camera images are processed for removing the fiducial objects located on the surface of the body segment depicted therein, which were used for computation of the 3D coordinates. The removal of the fiducial objects may be made after computation of the 3D coordinates, before and/or after assigning the 3D coordinates to the pixels to compute the voxels.

At 226, a 3D image is reconstructed by aggregating the voxels created from the pixels of the camera image and from voxels created from pixels of the ultrasound images in the common coordinate system. The 3D image depicts the surface of the body segment and tissues within the body segment located relative to the surface.

The common coordinate system may be the real-world coordinate system that depicts real-world distances and locations. The 3D image depicts the surface of the body segment and tissues within the body segment using real-world coordinates, distances, and relative locations. For example, a user may measure how deep a blood vessel is below an area of skin using the reconstructed 3D images. In another example, a user using the 3D image to guide a catheter into deep tissue may navigate using the reconstructed 3D image by moving the catheter in directions and/or distances to reach the target tissue as shown by the real-world coordinate system of the reconstructed 3D image.

At 228, one or more of the 3D reconstructed images with blood flow depicting the surface of the body, and/or segmented, are provided, for example, presented on display, stored in a storage device, and/or forwarded to another remote device.

A single 3D image that presents blood flow, the surface of the body, and is segmented, may be presented. Alternatively or additionally, a baseline 3D image may be presented, and the user may select one or more of: blood flow, surface, and segmentations, to be presented as additional data, for example, as overlays and/or integrated within the baseline 3D image. Alternatively or additionally, multiple images may be presented, each depicting different data, for example, side by side on a display. The multiple images may be selected from: depicting blood flow, depicting the surface, and depicting segmentations.

Referring now back to FIG. 12, which is a schematic depicting an example 3D image 1202 of a brachial artery computed based on camera images depicting a pattern on a surface of an arm of a subject and ultrasound images of the brachial artery, and 1204 which depicted the surface of the patient body.

Referring now back to FIG. 13, a schematic is provided that depicts an environment scene of a generation of a 3D image 1302 computed from camera images and ultrasound images according to an ultrasonic gel with randomly distributed fiducial objects 1304 located on the skin over an artery 1306 of a leg 1308 of a subject for which 3D image 1302 is being generated. An ultrasound probe 1310 that includes an ultrasound transducer 1312 captures ultrasound images and/or Doppler images 1318, e.g., in B-mode, Doppler-mode of artery 1306, and a camera 1314 connected to probe 1310, optionally via an add-on component 1316 as described herein, captures camera images of randomly distributed fiducial objects 1304 within the gel. Ultrasound images and/or Doppler images 1318 may be captured by a standard probe 1310 connected to a standard ultrasound workstation 1320 operated using standard ultrasound approaches and/or operated by a non-skilled user, as described herein. Surface image(s) 1322 of a surface of leg 1308 may be extracted from the camera image, as described herein. 3D image 1302 is computed from data 1324, including 3D coordinates computed for the ultrasound images using the camera images, as described herein, optional Doppler data assigned to the 3D coordinates, and optional surface image(s) 1322, as described herein. 3D image 1302 depicts a portion of artery 1306 that is larger than any single 2D artery, e.g., a stretch of the artery, the entire artery, with an optional indication of blood flow within multiple locations of artery 1306. 3D image 1302 may include a 3D reconstruction of surface image 1322 relative to artery 1306, enabling visualization of the location of artery 1306 within leg 1308 below the skin surface.

Referring now back to FIG. 2, at 230, other post-processing may be performed using the reconstructed 3D image(s).

Optionally, the reconstructed 3D image(s) is registered with another 3D anatomical image that depicts the body segment. The 3D anatomical image is captured by a 3D imaging modality device, such as CT and MRI. The registration may be performed at least according to features extracted from the surface of the body segment depicted in the reconstructed 3D image(s) and depicted in the 3D anatomical image. For example, registration is performed between the skin surfaces and may further be performed between internal blood vessels and/or other tissues.

Alternatively or additionally, the reconstructed images are fed as input into another processing application, e.g., surgical planning application, a neural network that diagnoses vascular pathologies.

At 232, one or more features described with reference to 204-230 may be iterated. The iterations may be performed by capturing additional ultrasound and camera images, gathering additional pixel and 3D coordinate data, and updating the reconstructed 3D image with the additional data to increase the resolution of the updated reconstructed 3D image. The resolution of the image may increase as the user moves the ultrasound probe and captures additional images.

Optionally, at 234, an add-on device is provided. The add-on device is used for capturing the ultrasound images and camera images, as described herein.

Referring now back to FIG. 14, a schematic depicting an add-on 1402 to an ultrasound probe 1404 for capturing camera images by a camera 1406 and an ultrasound transducer 1406 for capturing ultrasound images used to reconstruct a 3D image, is provided. Add-on 1402 is set to provide a fixed angle 1410, e.g., 7.2 degrees, or other values, between an axis 1412 of ultrasound transducer 1408 for capturing of ultrasound images and/or corresponds to an axis of probe 1404, and an axis 1414 of camera 1406 for capturing of camera images. A 3D pose ultrasound transducer 1406 may be computed based on the camera image(s) captured by camera 1406 according to known angle 1410. The 3D voxels corresponding to pixels the ultrasound image used to reconstruct the 3D image may be computed based on the computed pose of ultrasound transducer 1406, based on known angle 1410, as described herein.

Add-on 1402 includes a connector component 1416 sized and shaped to securely connect to probe 1404, for example, secured by friction, e.g., connector component 1416 includes an aperture sized to secure against an external perimeter of probe 1404, so that when the aperture is slide over probe 1404, the probe 1404 is secured within the aperture, screws, glue, formed as an integrated part of probe 1404, e.g., by injection molding, and/or clips.

A camera housing 1418 is connected to connector 1416. The camera housing 1418 is set at predefined angle 1410 relative to axis 1412, the connector component 1412, which corresponds to the axis of probe 1404. Camera 1406 is located within camera housing 1418. Camera 1406 captures camera image(s) at a predefined angle 1410 relative to the ultrasound image(s) captured by the ultrasound transducer 1408.

Optionally, add-on 1402 includes apertures sized and shaped for a cable 1420 of camera 1406 and/or a cable 1422 of probe 1404. The cables may connect to a computer for transmitting captures camera images and/or ultrasound images. The cables may be for connecting to a power source. Alternatively or additionally, aperture(s) are not necessarily required when camera 1406 and/or probe 1404 transmit images using a wireless interface and/or when batteries are used.

Optionally, add-on 1402 includes a light source, for example, located within camera housing 1418, and/or within camera 1406, and/or as another component. The light source may be set for emitting light at selected frequencies according to target fiducial objects suspended within an ultrasonic gel, as described herein, for example, ultraviolet light and/or selected frequencies to enhance fiducial objects made out of fluorescent material and/or material that enhances in response to UV light. The light source may be set at preselected angle 1410, corresponding to the angle 1410 of camera 1406, for transmitting light to the portion of the ultrasonic gel at the surface of the body being depicted in the camera images captured by camera 1406.

Referring now back to FIG. 15, which is a schematic depicting an exemplary add-on 1502 to an ultrasound probe, including a connector component 1516 sized and shaped for connecting to an ultrasound probe and camera housing 1518 set at a predefined angle relative to a long axis of the connector component 1516 which corresponds to a long axis of an ultrasound transducer of the probe. Schematic 1550 is a front-left view of add-on 1502. Schematic 1552 is a back-right view of add-on 1502.

Connector component 1516 includes a channel 1554 designed to slide over the handle of the probe. Multiple screw apertures 1556 designed to receive screws for securing add-on 1502 secured in place relative to the probe. It is noted that other securing mechanisms may be used, as described herein.

Camera housing 1518 includes a view aperture 1558 through which a lens of a camera located within camera housing 1518 captures camera images. Camera housing 1518 may include a camera cable aperture 1560 sized and shaped for positioning a cable connected to the camera. The cable may be connected to a computer for receiving the camera images. Alternatively, the cable may be for connecting to a power source. It is noted that when a wireless interface is used to transmit the images and/or batteries are used, cables and/or aperture 1560 are not necessarily required.

Referring now back to FIG. 16, which is a schematic of another exemplary implementation of an add-on 1602 to an ultrasound probe 1604. Add-on 1602 includes two camera housings 1618A-B that each includes a respective camera 1606A-B. i.e., camera 1606A in housing 1618A and camera 1606B in housing 1618B. Camera housings 1618A-B are connected to a connector component 1616 that securely connects add-on 1602 to ultrasound probe 1604, as described herein. Camera housings 1618A-B are each set at a predefined angle relative to the long axis of the connector component, to fix cameras 1606A-B at a predefined angle relative to the ultrasound probe 1604 and/or relative to ultrasound images captured by an ultrasound transducer 1608 of probe 1604, as described herein. The predefined angles may be the same for both cameras 1606A-B, or each camera 1606A-B may be set at a different predefined angle.

Optionally, camera housings 1618A-B and corresponding cameras 1606A-B are separated by about 90 degrees, or other value, perpendicular to a long axis of connector component 1616, i.e., a radial distance relative to the long axis of connector component 1616 is about 90 degrees. The 90-degree angle may be selected for capturing camera images of the same region of a surface of a body of a subject during sagittal or longitudinal orientation of the ultrasound transducer 1608. Other angles may be used, in which case the known angle is used to compute the relationship between the two images. For example, in a longitudinal examination, where a long axis of ultrasound transducer 1608 is placed in parallel to a long axis of the tissue, for example, along a length of a blood vessel, camera 1606B is set to capture camera images of fiducial objects randomly distributed in a viscous material, e.g., ultrasonography gel, located on the surface of the body, above the blood vessel. In a sagittal examination, where the long axis of ultrasound transducer 1608 is placed at some angle relative to the long axis of the tissue, for example, along a diameter of the blood vessel, camera 1606A is set to capture camera images of the same fiducial objects randomly distributed in the viscous material, e.g., ultrasonography gel, located at the same location on the surface of the body as captured by camera 1606B during the longitudinal examination. Capturing the fiducial objects randomly distributed in the viscous material during the different orientations of ultrasound transducer 1608 enables reconstruction of the 3D image of the tissue, e.g., blood vessel; these fiducial objects may add additional information for calculating the actual scale of the structure and motion of the transducer in world units. Optionally, add-on 1602 includes an inertial measurement unit (IMU) which is used alternatively or additionally to the analysis of relative changes in locations of the fiducial objects in subsequent camera images to compute the pose of the ultrasound transducer and/or pose of the camera and may add additional information for calculating the actual scale of the structure and motion of the transducer in world units.

Referring now back to FIGS. 21A-B, a schematic of another exemplary implementation of an add-on 2102 to an ultrasound probe 2104 is depicted. FIG. 21A depicts add-on 2102 from a front view. FIG. 21B depicts add-on 2102 from a rear view. Add-on 2102 includes two camera housings 2118A-B that each includes a respective camera 2106A-B, i.e., camera 2106A in housing 2118A and camera 2106B in housing 2118B. Camera housings 2118A-B are connected to an ergonomic holder component 2116 that securely connects add-on 2102 to ultrasound probe 2104, as described herein. For example, ultrasound probe 2104 is slid into compartment formed by add-on 2102 that has an internal size and/or shape that corresponds to an external size and/or shape of ultrasound probe 2104. Ultrasound probe 2104 may be held in place, for example, by clicking in place with clips that apply pressure, by friction from the internal walls of the compartment, by straps, and the like. Ergonomic holder 2116 may include a grip 2150 designed to be held against the palm of the hand of the user, and a ring or trigger like element 2152 designed for supporting a user's index finger.

Ergonomic holder 2116 is designed to provide the user with improved grip, enabling finer control and/or finer movement during the ultrasound scanning.

Camera housings 2118A-B are each set at a predefined angle relative to the long axis of the connector component, to fix cameras 2106A-B at a predefined angle relative to the ultrasound probe 2104 and/or relative to ultrasound images captured by an ultrasound transducer 2108 of probe 2104, as described herein. The predefined angles may be the same for both cameras 2106A-B, or each camera 2106A-B may be set at a different predefined angle. Camera 2106B has a detachable lens 2120, that can be separated from the camera 2106B itself, making it easier for the user to use different lens for certain types of body scans.

Optionally, camera housings 2118A-B and corresponding cameras 2106A-B are separated by about 90 degrees or other value, perpendicular to a long axis of connector component 2116, i.e., a radial distance relative to the long axis of connector component 2116 is about 90 degrees. The 90-degree angle may be selected for capturing camera images of the same region of a surface of a body of a subject during sagittal or longitudinal orientation of the ultrasound transducer 2108. Other angles may be used (for example, about 70 degrees or 80 degrees or 100 degrees or 110 degrees or other values), in which case the known angle is used to compute the relationship between the two images. For example, in a longitudinal examination, where a long axis of ultrasound transducer 2108 is placed in parallel to a long axis of the tissue, for example, along a length of a blood vessel, camera 2106B is set to capture camera images of fiducial objects randomly distributed in a viscous material, e.g., ultrasonography gel, located on the surface of the body, above the blood vessel. In a sagittal examination, where the long axis of ultrasound transducer 2108 is placed at some angle relative to the long axis of the tissue, for example, along a diameter of the blood vessel, camera 2106A is set to capture camera images of the same fiducial objects randomly distributed in the viscous material, e.g., ultrasonography gel, located at the same location on the surface of the body as captured by camera 2106B during the longitudinal examination. Capturing the fiducial objects randomly distributed in the viscous material during the different orientations of ultrasound transducer 2108 enables reconstruction of the 3D image of the tissue, e.g., blood vessel; these fiducial objects may add additional information for calculating the actual scale of the structure and motion of the transducer in world units. Optionally, add-on 2102 includes an inertial measurement unit (IMU) (not shown, as it may be an internal component) which is used alternatively or additionally to the analysis of relative changes in locations of the fiducial objects in subsequent camera images to compute the pose of the ultrasound transducer and/or pose of the camera and may add additional information for calculating the actual scale of the structure and motion of the transducer in world units.

Optionally, at 236, the add-on device is calibrated. The calibration may be performed for computing one or more calibrated transformations that map pixels of the ultrasound coordinate system to/from the camera coordinate system. The calibrated mappings may map pixels of the ultrasound images and/or Doppler data and/or B-mode represented in the ultrasound coordinate system to the camera coordinate system, and vice versa. The mapping is based on a calibrated relationship between the pose of the camera and the pose of the ultrasound transducer. The calibrated mapping is used for mapping the pixels of the Doppler and/or B-mode ultrasound images represented in the camera coordinate system to the 3D coordinates within the camera coordinate system.

Calibration may be performed using a specially designed apparatus that includes a box with ultrasonography gel, randomly spaced strings, and a nearby checkerboard pattern, or other patterns may be used. When the ultrasound transducer scans a silicon box, two images appear simultaneously: an ultrasound image of the strings cross-section inside the box and a camera image of the checkerboard. The two images relate to each other—the pose of the camera from the checkerboard correspond with a different pose of the transducer from the known strings immersed in the silicone. The relationship between the two images is determined with a calibration process that gathers several images from different checkerboard locations, and the corresponded US images are analyzed and compared to the ground truth, i.e., the angle and distance that are coerced by the 3D computer modeling. The outcome of the process provides a homogenous calibrated transformation for transforming the camera images' pose to the transducer's pose.

Calibration may be used based on a random version of strings without defined geometry and the use of a checkerboard. In another example, another calibration device is based on a simple box with an ultrasonography gel and holes and April tags. The camera's pose is based on an estimation protocol, which determines the pose of the camera relative to each of the detected April tags, which can be detected in the captured image. Simultaneously, the transducer captures both the top and the bottom of the box, which can be used to determine the homogenous transformation between the camera and the transducer.

Referring now back to FIG. 17, a schematic depicting an exemplary implementation of a calibration device 1752, e.g., corresponding to calibration device 152 described with reference to FIG. 1, is provided. Calibration device 1752 includes an ultrasound compartment 1760, including a first predefined ground truth pattern 1762, and camera compartment 164 including a second predefined ground truth pattern 1766.

Ultrasound compartment 1760 may be implemented as a box with an open upper side. Ground truth pattern 1762 may be a 3D pattern with defined 3D coordinates submerged in an ultrasound permeable medium, such as transparent silicon. Ground truth pattern 1762 may be, for example, poles arranged in various angles, and/or different objects having different shapes, slopes with coincidental protuberances, and/or angles, for example, a box, a sphere, a pyramid, a rectangle, arranged at different heights and/or orientations, and/or a random pattern. Alternatively, or additionally, ground truth pattern 1762 may be a 2D pattern, for example, a checkerboard pattern and/or a wire pattern. Ground truth pattern 1766 may be 2D and/or 3D, for example, a checkerboard pattern. The shapes of patterns 1762 and 1766 are predefined; for example, pattern 1762 is printed using a 3D printer, and checkerboard pattern 1766 is printed using a 2D printer.

Camera compartment 1762 may be positioned in proximity to ultrasound compartment 1760, optionally separated by a transduction positioning region 1768. The arrangement of camera compartment 1762, ultrasound compartment 1760, and transducer positioning region 1768 are selected for simultaneously, or near-simultaneously, capturing an ultrasound image depicting the first predefined 3D ground truth pattern 1762 by an ultrasound transducer located at transducer positioning region 1768 and a camera image depicting the second predefined ground truth pattern 1766 by a camera located within an add-on to the ultrasound probe disposed on a probe connected to the ultrasound transducer located at transducer positioning region 1768.

The following is exemplary pseudocode for calibration using calibration device 1752:

1. Init Both ultrasound transducer and camera
2. Collect several checkerboard images and B-Mode images from different orientations and positions
3. Locate strings position in transducer image and estimate camera pose in world coordinate system relative the checkerboard pattern
4. Find homogenous transformation between the transducer coordinate system and the camera by minimizing the relative distance between the actual position of the recorded strings positions and the 3D known positions.
5. Return computed transformation Reference is now made to FIG. 18, a schematic depicting another exemplary implementation of another calibration device 1852, e.g., corresponding to calibration device 152 described with reference to FIG. 1, is provided. Calibration device 1852 includes a single compartment 1854 including a common predefined 2D markers and/or 3D truth pattern 1856, which is placed on top of the single compartment 1854. Compartment 1854 may be shaped, for example, having a circular shaped surface. Compartment 1854 may be shaped, for example, as a semi-sphere, cylinder, or other shapes. Pattern 1856 may be arranged externally and/or around (e.g., in proximity to) a boundary (e.g., perimeter) of the sphere of compartment 1854, for example, indicators of the pattern 1856 are equally spaced along the outer perimeter of compartment 1854. Compartment 1854 includes (e.g., is filled with) an ultrasound permeable ultrasonography medium, for example, transparent silicon or ultrasonography gel. When the ultrasound transducer is placed on top of the compartment 1854, optionally approximately in the middle, the camera captures a camera image of pattern 1856, and the ultrasound transducer captures an ultrasound image (e.g., image 1890 is an example) of interior of compartment 1854 from a top surface, 1860, to a bottom surface, 1862. The ultrasound sound waves may pass the top surface 1860 without significant attenuation and maybe also pass through a hole(s), 1864 Hole(s) 1864 may be located with respect to compartment 1854, for example, on the top, bottom, and/or within (e.g., middle). Pattern 1856 may be made of a material with selected properties, for example, being enhanced under ultraviolet (UV) light and/or fluorescent, and may be made of high contrast printed calibration pattern.

The following is exemplary pseudocode for calibration using calibration device 1852:

1. Init Both transducer camera and the camera
2. Collect simultaneously several camera images of the markers and the transducer images from different orientations and positions
3. For each transducer image locate floor (UV pixels) position in US image, and for each corresponding camera image locate each marker position in world units
4. For each detected tag and for each UV floor pixel compute the estimated floor depth based on homogeneous transformation from UV image to camera pose in the tag coordinates system
5. Find a homogeneous transformation that minimizes the relative distance between the actual known depth of the floor from the top surface and the estimated depth based on the above transformation (US image to world coordinates).
6. Return computed transform Optionally, for calibration of the IMU, use the IMU measurement and the camera recorded orientation simultaneously and use the gravity as the Z component of the IMU coordinate system.

Referring now back to FIG. 3, at 302, a viscous material at least a portion of which is fluid, optionally an ultrasonography gel, that includes fiducial objects randomly distributed in its volume and spaced apart by random distances, is applied to a surface of a body segment of an individual at a location corresponding to a blood vessel of interest.

When the material is an ultrasonography gel, the gel may be applied to a wider area of the skin and used in a standard manner to obtain ultrasound images.

At 304, a probe of an ultrasound transducer with an add-on component including one camera or more cameras is maneuvered along the surface of the body. Ultrasound images of the blood vessel within the body and camera images depicting the surface of the body segment and depicting the fiducial objects are captured, optionally simultaneously.

At 306, one or more 3D images are reconstructed from the ultrasound images, and an analysis of the camera images is presented on display.

Optionally, the 3D image depicts visual indications of blood flow at multiple regions within the blood vessel. Alternatively or additionally, the 3D image is segmented according to tissue types. Alternatively or additionally, the 3D image depicts the skin of the body segment and the blood vessel within a common real-world coordinate system representing real-world coordinates, wherein diagnosing the vascular pathology based on the reconstruction of the 3D image of the blood vessel relative to the surface of the body segment is further based on blood flow of the blood vessel depicted by the 3D image At 308, the 3D image(s) are analyzed. The analysis may be made manually by visual inspection and/or measurements and/or automatically by feeding the 3D image into a machine learning process, e.g., neural network, that generates an outcome indicating the diagnosis.

At 310, the vascular pathology is diagnosed based on the analysis of the 3D image. For example, stenosis in the blood vessel.

At 312, the vascular pathology is treated during an open surgical and/or catheterization procedure. The introduction, navigation, and/or treatment may be guided by the 3D image, for example, according to distances and/or relative locations depicted by the real-world coordinate system in which the skin and blood vessel of the 3D image is presented. Exemplary treatments include: stent delivered by a catheter, balloon inflation, ablation, drug injection, and manual surgical excision and/or repair.

At 314, the effectiveness of the vascular treatment may be assessed based on 3D images acquired after the treatment. For example, analyzing segmentation of the 3D image to determine whether a plaque was fully removed from the artery and/or to determine whether blood flow patterns returned to normal.

At 316, one or more features described with reference to 302-316 are iterated.

Optionally, iterations are performed by re-maneuvering the probe over the surface of the body for, e.g., simultaneously, capturing ultrasound images of the blood vessel depicting the treated vascular pathology, and analyzing the treated vascular pathology in another 3D reconstruction of the blood vessel created from the ultrasound images and the camera images captured during the re-maneuvering of the probe and re-treating the treated vascular pathology when the treated vascular pathology is determined to require another treatment procedure based on the another 3D reconstruction.

Alternatively or additionally, iterations are performed by repeatedly maneuvering the ultrasound transducer within a sub-region of the surface corresponding to the vascular pathology at an axial and/or longitudinal orientation of the ultrasound transducer to capture multiple ultrasound images of the vascular pathology at different angles and distances. A resolution of the 3D image, optionally of the vascular pathology, increases with an increased number of maneuvers of the ultrasound transducer over the sub-region.

Alternatively or additionally, iterations are performed based on code that analyzes data to detect a disease segment, e.g., higher velocity blood low, a stent, high calcium content. In response to the detection, an indication may be provided to the user to repeatedly scan the segment to increase the data to obtain higher resolution imaging of the diseased segment, for example, a beep, an audio message, a text message presented on display, and/or a video. Optionally, the code monitors the amount of data obtained to detect when sufficient data has been collected to generate a 3D image of a target high resolution, and another indication may be provided to the user to stop the ultrasound scans and/or move to the next region of the body to be scanned.

Referring now back to FIG. 19, a schematic 1902 depicting a standard vascular treatment using existing approaches, and a schematic 1904 depicting a vascular treatment using the 3D image created from ultrasound and camera images, is provided. As depicted in schematic 1902, a standard process, for example, for treating a vascular pathology of a leg that may lead to poor blood flow in the foot, may include, a standard Doppler of the leg. A CTA which may require a 2-day admission may be performed. An angiography procedure may be performed 1-2 weeks later to treat the vascular pathology, which may require a 3-day admission. Results of the procedure may be obtained by a 1-2 month follow-up. In contrast, schematic 1904 depicts how real-time 3D images of the leg vascular may be created, before, during treatment, e.g., to guide a catheter into the blood vessel, and after treatment, e.g., to evaluate effects of the vascular treatment, which may enable same day, and/or 2-day admissions.

FIG. 20 depicts a process for computing the estimated blood flow velocity field 2004, by using a computational fluid dynamic simulation, 2010, with a priori 3D model of the artery, 2006, which integrate as boundary condition blood flow measurements 2006, which may be measured by a Doppler mode of an ultrasound system from various positions, and by place accordingly within the corresponding 3D known model of the artery 2006, in the same coordinate system and the same volume 2002.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant viscous materials and fiducial objects will be developed and the scope of the terms viscous materials and fiducial objects are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method for reconstructing a 3D image depicting blood flow in a blood vessel of an individual, comprising:

obtaining Doppler ultrasound images depicting a blood vessel with blood flowing therein and measurement of blood flow in a region of the blood vessel, and 2D camera images captured by a camera depicting a plurality of fiducial objects randomly distributed within a viscous material and spaced apart by random distances on a surface of a body segment of the individual, wherein the Doppler ultrasound images include at least one Doppler ultrasound image, and the 2D camera images include at least one 2D camera image;

computing 3D coordinates within a world coordinate system for pixels of each of the Doppler ultrasound images using an external reference of an ultrasound transducer pose computed by analysis of relative changes in locations of the plurality of fiducial objects within sequential 2D camera images; and computing a respective estimated blood flow for each of a plurality of pixels of the Doppler ultrasound images at a plurality of locations within the blood vessel;

reconstructing a 3D image from 3D voxels computed from the 3D coordinates of pixels of the Doppler ultrasound images, including respective estimated blood flow, wherein the 3D image depicts an anatomical image of the blood vessel and depicts blood flow.

2. The computer-implemented method of claim 1, wherein the 3D coordinates are further computed by correcting for actual scale to the world coordinate system by using a size of the fiducial object and/or by adding information from other sensors selected from a group consisting of: an inertial measurement unit, and another camera.

3. The computer-implemented method of claim 1, wherein the 3D image further comprises voxels computed from a 3D point cloud or mesh depicting the surface of the body segment of the individual.

4. The computer-implemented method of claim 1, wherein computing 3D coordinates for pixels of each of the Doppler ultrasound images, comprises:

computing a pose of the camera in a camera coordinate system relative to the world coordinate system by analyzing relative changes in locations of the plurality of fiducial objects within sequential 2D camera images;

applying a calibrated mapping for mapping pixels of the ultrasound images represented in an ultrasound coordinate system to the camera coordinate system, wherein the calibrated mapping is based on a predefined transformation between the pose of the camera and a pose of an ultrasound transducer; and mapping the pixels of the ultrasound images represented in the camera coordinate system to the 3D coordinates within the world coordinate system.

5. The computer-implemented method of claim 1, wherein computing the respective estimated blood flow comprises an estimated blood flow computed from the Doppler ultrasound image captured by the ultrasound transducer located at an angle to a vector denoting a direction of the blood vessel in which the blood flow is measured further comprising correcting the estimated blood flow for the angle to obtain an estimated actual blood flow.

6. The computer-implemented method of claim 5, wherein correcting comprises identifying an elliptical-shaped boundary of the blood vessel, computing a transformation of the elliptical shape to a circle, and applying the transformation for projecting the measured blood flow velocity vector to obtain the actual blood flow.

7. The computer-implemented method of claim 5, further comprising computing an estimate of a longitudinal axis of the blood vessel based on an aggregation of a plurality of 3D points obtained from respective planes of acquisition of each of a plurality of Doppler ultrasound images, computing a current tangent to the longitudinal axis, and wherein correcting comprises correcting the measurement of blood flow based on an angle between the tangent and a normal to the respective plane of acquisition denoted by the tangent.

8. The computer-implemented method of claim 5, further comprising computing an estimate of a blood flow within a precalculated 3D artery object and using computational fluid dynamics simulation and 3D points obtained from respective planes of acquisition of each of a plurality of Doppler ultrasound images for computing an estimate of blood flow within the 3D artery object.

9. The computer-implemented method of claim 5, further comprising: for each respective 3D voxel, storing a plurality of initially estimated blood flow values and a corresponding normal to a plane of the ultrasound transducer at which a respective Doppler US image used to compute the respective initial estimated blood flow is captured, estimating actual blood flow in each voxel based on minimizing a projection error between a recorded blood flow velocity vector and an assumed flow velocity vector.

10. The computer-implemented method of claim 9, further comprising:

obtaining volumetric flow within the blood vessel on a sagittal view at a specific location for a plurality of cardiac cycles, and computing an average volumetric flow over the plurality of cardiac cycles;

computing a gamma value denoting a real number in a range of −1 to 1 to correct the average volumetric flow and the estimated actual blood flow;

computing a cosine angle by using an inverse of the gamma value; and correcting the average volumetric flow using the cosine angle and a dot product between estimated blood flow and real blood flow.

11. The computer-implemented method of claim 1, further comprising:

alternating between (i) obtaining the Doppler ultrasound images and 2D camera images and (ii) obtaining second images comprising B-mode ultrasound images and 2D camera images;

computing in the world coordinate system, 3D coordinates for pixels of each of the B-mode ultrasound images;

wherein reconstructing the 3D image comprises reconstructing the 3D image from 3D voxels in the world coordinate system computed by aggregating the 3D coordinates of pixels of the B-mode ultrasound images and the Doppler ultrasound images including respective estimated blood flow, wherein the 3D image depicts the anatomical image of the blood vessel created from the aggregation of 3D voxels obtained from pixels of the B-mode and depicts the blood flow in association with the 3D voxels obtained from pixels of the B-mode.

12. The computer-implemented method of claim 1, wherein the respective estimated blood flow is depicted as color coding of the 3D voxels of the 3D image corresponding to the plurality of locations within the blood vessel, wherein pixels of the Doppler ultrasound images are color-coded denoting blood flow, and further comprising segmenting the colored pixels, wherein the 3D image is reconstructed from 3D voxels corresponding to the segmented color pixels.

13. The computer-implemented method of claim 1, wherein the respective estimated blood flow of the 3D voxels is selected as maximal values over an imaging time interval during which the Doppler ultrasound images depicting a region within the blood vessel corresponding to the 3D voxels is captured.

14. The computer-implemented method of claim 1, wherein a plurality of Doppler ultrasound images used to compute the 3D voxels are captured over an imaging time interval depicting variation in blood flow, and wherein the reconstructed 3D image includes, for the 3D voxels, a respective indication of variation in blood flow over the imaging time interval.

15. The computer-implemented method of claim 12, wherein the reconstructed 3D image is presented as a video over an imaging time interval by varying the indication of blood flow corresponding to the 3D voxels over the imaging time interval.

\* \* \* \* \*